(12) United States Patent
Berger et al.

(10) Patent No.: US 8,916,600 B2
(45) Date of Patent: *Dec. 23, 2014

(54) PHENYL AND BENZODIOXINYL SUBSTITUTED INDAZOLES DERIVATIVES

(75) Inventors: Markus Berger, Berlin (DE); Hartmut Rehwinkel, Berlin (DE); Jan Dahmén, Lund (SE); Anders Eriksson, Lund (SE); Thomas Hansson, Lund (SE); Nafizal Hossain, Lund (SE); Per Tomas Klingstedt, Lund (SE); Matti Lepistö, Lund (SE); Stinabritt Nilsson, Lund (SE); Martin Hemmerling, Lund (SE); Karl Edman, Mölndal (SE)

(73) Assignees: Astrazeneca AB, Södertalje (SE); Bayer Pharma Aktiengesellschaft, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/490,204

(22) Filed: Jun. 6, 2012

(65) Prior Publication Data

US 2012/0302617 A1 Nov. 29, 2012

Related U.S. Application Data

(63) Continuation of application No. 12/468,561, filed on May 19, 2009, now Pat. No. 8,211,930.

(60) Provisional application No. 61/054,616, filed on May 20, 2008, provisional application No. 61/080,312, filed on Jul. 14, 2008, provisional application No. 61/144,776, filed on Jan. 15, 2009.

(51) Int. Cl.
*A61K 31/416* (2006.01)
*C07D 231/54* (2006.01)
*C07D 405/14* (2006.01)
*C07D 409/12* (2006.01)
*C07D 231/56* (2006.01)
*C07D 409/14* (2006.01)
*C07D 403/12* (2006.01)
*C07D 401/12* (2006.01)
*C07D 405/12* (2006.01)
*C07D 401/14* (2006.01)
*C07D 403/10* (2006.01)
*C07D 413/12* (2006.01)

(52) U.S. Cl.
CPC ............ *C07D 403/10* (2013.01); *C07D 409/12* (2013.01); *C07D 231/56* (2013.01); *C07D 409/14* (2013.01); *C07D 403/12* (2013.01); *C07D 401/12* (2013.01); *C07D 405/12* (2013.01); *C07D 405/14* (2013.01); *C07D 401/14* (2013.01); *C07D 413/12* (2013.01)
USPC .......... 514/406; 548/362.5; 514/403

(58) Field of Classification Search
CPC ... A61K 31/416; C07D 231/54; C07D 405/14
USPC .......... 548/356.1, 360.1, 362.5; 514/403, 406
See application file for complete search history.

(56) References Cited

U.S. PATENT DOCUMENTS

| | | | |
|---|---|---|---|
| 3,992,441 A | 11/1976 | Helland | |
| 4,443,477 A | 4/1984 | Witte et al. | |
| 4,948,809 A | 8/1990 | Witte et al. | |
| 5,861,401 A | 1/1999 | Bradbury | |
| 6,323,199 B1 | 11/2001 | Lehmann et al. | |
| 7,297,709 B2 | 11/2007 | Dai et al. | |
| 7,544,690 B2 | 6/2009 | Sekiguchi et al. | |
| 7,728,030 B2 | 6/2010 | Berger et al. | |
| 8,030,340 B2 | 10/2011 | Berger et al. | |
| 8,082,858 B2 | 12/2011 | Yoshizawa | |
| 8,143,290 B2 | 3/2012 | Berger et al. | |
| 8,211,930 B2 * | 7/2012 | Berger et al. ................. | 514/406 |
| 2004/0235892 A1 | 11/2004 | Dai et al. | |
| 2007/0060633 A1 | 3/2007 | Mugge et al. | |

(Continued)

FOREIGN PATENT DOCUMENTS

| | | |
|---|---|---|
| CN | 101094832 | 12/2007 |
| EP | 0031954 | 7/1981 |

(Continued)

OTHER PUBLICATIONS

Alovero et al., "Mode of Action of Sulfanilyl Fluoroquinolones", *Antimicrob. Agents Chemother.* 42(6):1495-1498 (1998).
Berger et al. (2008): STN International HCAPLUS database, Columbus (OH), accession No. 2008:771134.
Bradbury et al., "New Non-Peptide Endothelin-A Receptor Antagonists: Synthesis, Biological Properties, and Structure-Activity Relationships of 5-(Dimethylamino)-*N*-pyridyl-, -*N*-pyrimidinyl-*N*-pyridazinyl-, and—*N*-pyrazinyl-1-naphthalenesulfonamides", *J. Med. Chem.* 40:996-1004 (1997).
Clark et al., "1*H*-Pyrazolo[3,4-*g*]hexahydro-isoquinolines as selective glucocorticoid receptor antagonists with high functional activity", *Bioorg. Med. Chem. Lett.* 18:1312-1317 (2008).

(Continued)

*Primary Examiner* — Golam M M Shameem
(74) *Attorney, Agent, or Firm* — Ropes & Gray LLP; Anita Varma; Yang Xu

(57) ABSTRACT

A compound of formula Ia:

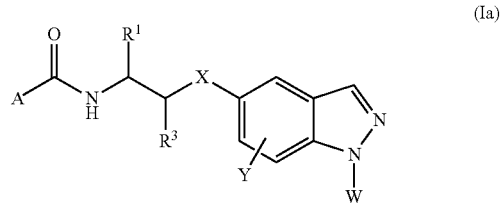

(Ia)

The present invention relates to novel indazolyl derivatives, to pharmaceutical compositions comprising such derivatives, to processes for preparing such novel derivatives and to the use of such derivatives as medicaments.

4 Claims, No Drawings

(56) References Cited

U.S. PATENT DOCUMENTS

| | | |
|---|---|---|
| 2007/0265326 A1 | 11/2007 | Biggadike et al. |
| 2008/0207721 A1 | 8/2008 | Berger et al. |
| 2008/0214641 A1 | 9/2008 | Berger et al. |
| 2009/0093485 A1 | 4/2009 | Bladh et al. |
| 2009/0124607 A1 | 5/2009 | Bladh et al. |
| 2009/0170898 A1 | 7/2009 | Bengtsson et al. |
| 2010/0080786 A1 | 4/2010 | Dahmen et al. |
| 2010/0087489 A1 | 4/2010 | Dahmen et al. |
| 2010/0197644 A1 | 8/2010 | Berger et al. |
| 2011/0071194 A1 | 3/2011 | Berger et al. |
| 2011/0130426 A1 | 6/2011 | Bladh et al. |
| 2012/0065173 A1 | 3/2012 | Berger et al. |

FOREIGN PATENT DOCUMENTS

| | | |
|---|---|---|
| EP | 0201735 | 11/1986 |
| EP | 0261539 | 3/1988 |
| EP | 0558258 | 9/1993 |
| EP | 0569193 | 11/1993 |
| EP | 0610896 | 8/1994 |
| EP | 0679641 | 11/1995 |
| EP | 0947500 | 10/1999 |
| EP | 0976722 | 2/2000 |
| EP | 1190710 | 3/2002 |
| EP | 1447401 | 8/2004 |
| GB | 0607840.6 | 4/2006 |
| WO | WO95/02580 | 1/1995 |
| WO | WO95/03279 | 2/1995 |
| WO | WO95/33461 | 12/1995 |
| WO | WO96/06822 | 3/1996 |
| WO | WO96/36595 | 11/1996 |
| WO | WO99/33786 | 7/1999 |
| WO | WO99/38845 | 8/1999 |
| WO | WO01/24786 | 4/2001 |
| WO | WO01/46172 | 6/2001 |
| WO | WO02/20474 | 3/2002 |
| WO | WO02/28820 | 4/2002 |
| WO | WO03/028641 | 4/2003 |
| WO | WO03/076401 | 9/2003 |
| WO | WO03/086294 | 11/2003 |
| WO | WO03/099773 | 12/2003 |
| WO | WO2004/018414 | 3/2004 |
| WO | WO2004/019935 | 3/2004 |
| WO | WO2004/050631 | 6/2004 |
| WO | WO2004/073634 | 9/2004 |
| WO | WO2004/089913 | 10/2004 |
| WO | WO2004/110418 | 12/2004 |
| WO | WO2005/004810 | 1/2005 |
| WO | WO2005/060963 | 7/2005 |
| WO | WO2005/077895 | 8/2005 |
| WO | WO2005/086904 | 9/2005 |
| WO | WO2005/123688 | 12/2005 |
| WO | WO2006/046914 | 5/2006 |
| WO | WO2006/046916 | 5/2006 |
| WO | WO2006/108699 | 10/2006 |
| WO | WO2006/135826 | 12/2006 |
| WO | WO2006/138373 | 12/2006 |
| WO | WO2007/046747 | 4/2007 |
| WO | WO2007/054294 | 5/2007 |
| WO | WO2007/114763 | 10/2007 |
| WO | WO2007/122165 | 11/2007 |
| WO | WO2008/008882 | 1/2008 |
| WO | WO2008/043788 | 4/2008 |
| WO | WO2008/043789 | 4/2008 |
| WO | WO2008/051532 | 5/2008 |
| WO | WO2008/057856 | 5/2008 |
| WO | WO2008/057857 | 5/2008 |
| WO | WO2008/063116 | 5/2008 |
| WO | WO2008/070507 | 6/2008 |
| WO | WO2008/076048 | 6/2008 |
| WO | WO2008/079073 | 7/2008 |
| WO | WO2008/124665 | 10/2008 |
| WO | WO2008/124745 | 10/2008 |
| WO | WO2008/135578 | 11/2008 |
| WO | WO2009/050218 | 4/2009 |
| WO | WO2009/050220 | 4/2009 |
| WO | WO2009/050221 | 4/2009 |
| WO | WO2009/050243 | 4/2009 |
| WO | WO2009/050244 | 4/2009 |
| WO | WO2009/062950 | 5/2009 |
| WO | WO2009/074590 | 6/2009 |
| WO | WO2009/108525 | 9/2009 |
| WO | WO2009/111214 | 9/2009 |

OTHER PUBLICATIONS

Gaedcke et al., "Structure dependence of antiplasmodic activity of 3-IN-(4'—amidosulphonylphenyl)amin~methyl quinoline", *Arch. Pharm* (Weinheim) 313:166-173 (1930).

Jansen et al., "Hydantoin-Substituted 4,6-Dichloroindole-2-carboxylic Acids as Ligands with High Affinity for the Glycine Building Site of the NMDA Receptor", *J. Med. Chem.* 46:64-73 (2003).

Mohler et al., "Dissociated non-steroidal glucocorticoids: tuning out untoward effects", *Expert Opin. Ther. Patents* 17:37-58 (2007).

Mohler et al., "Non-steroidal glucocorticoid receptor antagonists: the race to replace RU-486 for anti- glucocorticoid therapy", *Expert Opin. Ther. Patents* 17:59-81 (2007).

Schäcke et al., "Dissociated non-steroidal glucocorticoid receptor modulators: an update on new compounds", *Expert Opin. Ther. Patents* 18:339-352 (2008).

STN International file Registry: RN 321722-44-5, RN 321704-10-3, RN 321704-02-3, RN 321703-82-6, RN 321703-77-9, RN 321703-75-7.

USPTO Non-Final Office Action in U.S. Appl. No. 11/986,555, mailed May 12, 2009, 12 pages.

Fish & Richardson P.C., Amendment in Reply to Action of May 12, 2009 in U.S. Appl. No. 11/986,555, filed Aug. 12, 2009, 42 pages.

USPTO Notice of Allowance in U.S. Appl. No. 11/986,555, mailed Nov. 19, 2009, 11 pages.

Fish & Richardson P.C., RCE, Amendment and IDS in reply to Notice of Allowance of Nov. 19, 2009 in U.S. Appl. No. 11/986,555, filed Feb. 17, 2010, 9 pages.

USPTO Notice of Allowance in U.S. Appl. No. 11/986,555, mailed Jun. 2, 2011, 14 pages.

Fish & Richardson P.C., Response to Notice of Allowance of Jun. 2, 2011 U.S. Appl. No. 11/986,555, filed Sep. 1, 2011, 2 pages.

USPTO Notice of Allowance in U.S. Appl. No. 12/005,066, mailed Mar. 24, 2009, 10 pages.

Fish & Richardson P.C., RCE and Interview Summary in reply to Notice of Allowance of Mar. 24, 2009 in U.S. Appl. No. 12/005,066, filed Jun. 19, 2009, 6 pages.

USPTO Notice of Allowance in U.S. Appl. No. 12/005,066, mailed Sep. 9, 2009, 6 pages.

Fish & Richardson P.C., RCE and IDS in reply to Notice of Allowance of Sep. 9, 2009 in U.S. Appl. No. 12/005,066, filed Nov. 10, 2009, 5 pages.

USPTO Notice of Allowance in U.S. Appl. No. 12/005,066, mailed Jan. 13, 2010, 8 pages.

Fish & Richardson P.C., Response to Notice of Allowance of Jan. 13, 2010 in U.S. Appl. No. 12/005,066, filed Apr. 13, 2010, 2 pages.

USPTO Non-Final Office Action in U.S. Appl. No. 12/643,504, mailed Sep. 2, 2010, 8 pages.

USPTO Non-Final Office Action in U.S. Appl. No. 12/959,027, mailed Jul. 21, 2011, 15 pages.

USPTO Non-Final Office Action in U.S. Appl. No. 12/295,092, mailed Jun. 30, 2011, 7 pages.

USPTO Non-Final Office Action in U.S. Appl. No. 12/468,494, mailed Jun. 28, 2011, 11 pages.

USPTO Non-Final Office Action in U.S. Appl. No. 12/468,561, mailed Jun. 15, 2011, 10 pages.

Fish & Richardson P.C., Amendment in Reply to Action of Jun. 15, 2011 in U.S. Appl. No. 12/468,561, filed Oct. 28, 2011, 18 pages.

USPTO Final Office Action in U.S. Appl. No. 12/468,561, mailed Nov. 30, 2011, 15 pages.

Fish & Richardson P.C., Amendment in Reply to Action of Nov. 30, 2011 in U.S. Appl. No. 12/468,561, filed Feb. 21, 2012, 11 pages.

USPTO Notice of Allowance in U.S. Appl. No. 12/468,561, mailed Mar. 2, 2012, 10 pages.

(56) References Cited

OTHER PUBLICATIONS

Fish & Richardson P.C., Response to Notice of Allowance of Mar. 2, 2012 in U.S. Appl. No. 12/468,561, filed Jun. 4, 2012, 2 pages.

USPTO Restriction Requirement in U.S. Appl. No. 13/224,382, mailed Mar. 21, 2012, 6 pages.

Fish & Richardson P.C., Amendment in Reply to Action of Jul. 21, 2011 in U.S. Appl. No. 12/959,027, filed Oct. 21, 2011, 8 pages.

USPTO Notice of Allowance in U.S. Appl. No. 12/959,027, mailed Nov. 3, 2011, 9 pages.

Fish & Richardson P.C., Response to Notice of Allowance of Nov. 3, 2011 in U.S. Appl. No. 12/959,027, filed Feb. 2, 2012, 2 pages.

Fish & Richardson P.C., Amendment in Reply to Action of Jun. 28, 2011 in U.S. Appl. No. 12/468,494, filed Dec. 8, 2011, 18 pages.

USPTO Final Office Action in U.S. Appl. No. 12/468,494, mailed Dec. 27, 2011, 12 pages.

Ashton et al., "Structure-activity relationships of adenosines with heterocyclic $N^6$-substituents," Bioorg Med Chem Lett 17 (2007) pp. 6779-6784.

Dehmlow et al., "(S)-3-Aminothiolane: A New Chiral Building Block," Synthesis Oct. 1992, pp. 947-949.

Necela et al., "Crystallization of the human glucocorticoid receptor ligand binding domain: a step towards selective glucocorticoids," BM, Cidlowski, JA, Trends Pharmacol Sci, 24:58, 2003.

Remington's Pharmaceutical Sciences 1970, Part VIII Pharmaceutical Preparation and Their manufacture, p. 1463-1477.

Yin et al., "Highly Diastereoselective Catalytic Meerwein-Ponndorf-Verley Reductions," J. Org. Chem., 71, 840-843 (2006).

\* cited by examiner

PHENYL AND BENZODIOXINYL SUBSTITUTED INDAZOLES DERIVATIVES

CROSS REFERENCE TO RELATED APPLICATIONS

This application is a continuation of U.S. application Ser. No. 12/468,561, filed on May 19, 2009 now U.S. Pat. No. 8,211,930, which claims the benefit of U.S. Provisional Application No. 61/054,616, filed on May 20, 2008; U.S. Provisional Application No. 61/080,312, filed on Jul. 14, 2008; and U.S. Provisional Application No. 61/144,776, filed on Jan. 15, 2009, each of these prior applications is incorporated herein by reference in its entirety.

The present invention relates to novel indazolyl derivatives, to pharmaceutical compositions comprising such derivatives, to processes for preparing such novel derivatives and to the use of such derivatives as medicaments (for example in the treatment of an inflammatory disease state).

Sulphonamide derivatives are disclosed as anti-inflammatories in WO 2004/019935 and WO 2004/050631. Pharmaceutically active sulphonamides are also disclosed in Arch. Pharm, (1980) 313 166-173, J. Med. Chem. (2003) 46 64-73, J. Med. Chem. (1997) 40 996-1004, EP 0031954, EP 1190710 (WO 200124786), U.S. Pat. No. 5,861,401, U.S. Pat. No. 4,948,809, U.S. Pat. No. 3,992,441 and WO 99/33786.

It is known that certain non-steroidal compounds interact with the glucocorticoid receptor (GR) and, as a result of this interaction, produce a suppression of inflammation (see, for example, U.S. Pat. No. 6,323,199). Such compounds can show a clear dissociation between anti-inflammatory and metabolic actions making them superior to earlier reported steroidal and non-steroidal glucocorticoids. The present invention provides further non-steroidal compounds as modulators (for example agonists, antagonists, partial agonists or partial antagonists) of the glucocorticoid receptor. {Modulators of the glucocorticoid receptor are disclosed in WO 2007/122165, WO 2008/076048 and WO 2008/043788.}

Compared to the known compounds the compounds of the present invention are contemplated to have improved properties such as selectivity, efficacy and/or crystallinity over the known compounds.

These new compounds are also contemplated to have an improved low LogD and thus an improved distribution volume in vivo. The systemic exposure of the compounds is also expected to be improved. Further the compounds are contemplated to have a lower melting point and improved crystallinity compared to the known compounds.

The compounds of the present invention are contemplated to have both an improved binding as well as improved crystallinity compared to the known compounds.

The present invention provides a compound of formula Ib:

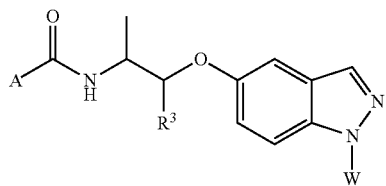

wherein:
A is $C_{1-4}$alkyl, $C_{1-4}$alkoxy or $C_{1-4}$haloalkyl;
$R^3$ is $C_{5-10}$heteroaryl;
W is phenyl substituted by —C(O)NR$^7$R$^8$;
$R^7$ is hydrogen or $C_{1-4}$alkyl;
$R^8$ is selected from hydrogen,
$C_{1-6}$alkyl (optionally substituted by one or two groups selected from hydroxyl, $C_{5-10}$aryl and $C_{5-10}$heteroaryl), $C_{3-7}$cycloalkyl (optionally substituted by hydroxyl), and $C_{5-10}$heterocyclyl (optionally substituted by one or two groups selected from hydroxyl and oxo);
or a pharmaceutically acceptable salt thereof.

One embodiment of the present invention provides a compound of formula Ia

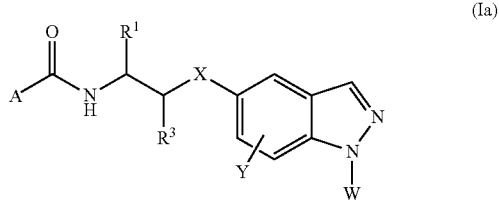

wherein:
A is $C_{1-6}$alkyl, $C_{1-6}$alkoxy, $C_{3-7}$cycloalkyl, $C_{1-6}$haloalkyl, $C_{1-6}$alkylthio, $C_{1-6}$alkylC(O), $C_{1-6}$alkyloxyC(O), NR$^5$R$^6$, NR$^5$R$^6$C(O) or $C_{5-10}$heteroaryl, all optionally substituted by one or more substituents independently selected from halo, cyano, hydroxyl, $C_{1-4}$alkyl, $C_{1-4}$alkoxy and $C_{1-4}$haloalkyl;
$R^5$ and $R^6$ are independently selected from hydrogen, $C_{1-6}$alkyl, $C_{3-7}$cycloalkyl, $C_{1-6}$alkylC(O) and $C_{3-7}$cycloalkylC(O), or $R^5$ and $R^6$ might form a ring with the nitrogen to which they are attached;
$R^1$ is hydrogen, $C_{1-4}$alkyl, $C_{1-4}$hydroxyallyl, $C_{1-4}$alkyl OC$_{1-4}$alkyl, $C_{1-4}$alkylthioC$_{1-4}$alkyl or $C_{1-4}$haloalkyl;
$R^3$ is $C_{5-10}$aryl, $C_{5-10}$arylC$_{1-4}$alkyl, $C_{5-10}$arylO, $C_{5-10}$arylC$_{1-4}$alkoxy, $C_{5-10}$aryloxyC$_{1-4}$alkyl, $C_{5-10}$heteroaryl, $C_{5-10}$heteroarylC$_{1-4}$alkyl, $C_{5-10}$heteroarylC$_{1-4}$alkoxy or $C_{5-10}$heteroaryoxyC$_{1-4}$alkyl, all of which are unsubstituted or optionally substituted by one or more substituents independently selected from B;
B is hydroxyl, halo, cyano, $C_{1-4}$alkyl, $C_{1-4}$alkoxy, $C_{1-3}$hydroxyalkyl, $C_{1-4}$alkoxyC$_{1-4}$alkyl, $C_{3-6}$cycloalkyloxyC$_{1-4}$alkyl, $C_{3-6}$cycloalkyloxy, $C_{3-6}$cycloalkylthioC$_{1-4}$alkyl, $C_{3-6}$cycloalkylthio, $C_{1-3}$alkylS(O)$_k$C$_{1-4}$alkyl, $C_{1-3}$alkylS(O)$_k$, $C_{1-4}$haloalkyl or $C_{1-4}$haloalkoxy, or B is one of the following groups which are linked to adjacent carbons on an aryl or heteroaryl ring (CH$_2$)$_t$OC$_{1-4}$alkylenylO(CH$_2$)$_v$ or (CH$_2$)$_t$O(CH$_2$)$_v$;
k is 0, 1 or a compound according to claim 2;
t and v are, independently, 0, 1, 2 or 3, and t and v are not both 0;
X is O or NH;
W is phenyl substituted by one or more substituents independently selected from (CH$_2$)$_n$C(O)NR$^7$R$^8$, (CH$_2$)$_n$NR$^9$C(O)R$^8$ or (CH$_2$)$_n$C(O)NR$^9$(CR$^{14}$R$^{15}$)C(O)NR$^7$R$^8$; and W is optionally further substituted by halogen or $C_{1-4}$alkyl;
$R^7$ is hydrogen or $C_{1-4}$ alkyl;
$R^8$ and $R^9$ are, independently, hydrogen, $C_{1-4}$ alkyl (optionally substituted by one or two groups selected from hydroxyl, $C_{1-4}$ alkoxy, NH$_2$, oxo, C(O)NR$^{10}$R$^{11}$, NR$^{10}$C$_{1-4}$ alkyl, C(O)NR$^{10}$C$_{1-4}$ alkyl, NR$^{10}$C(O)C$_{1-4}$ alkyl, $C_{1-4}$ alkylthio, $C_{5-10}$heterocyclyl, $C_{5-10}$aryl or $C_{5-10}$heteroaryl), $C_{3-7}$cycloalkyl (optionally substituted by C(O)NH$_2$), $C_{5-10}$heterocyclyl, $C_{5-10}$aryl, $C_{5-10}$heteroaryl or C(O)NR$^{10}$R$^{11}$; $C_{5-10}$aryl or $C_{5-10}$heteroaryl are optionally substituted by halogen, $C_{1-4}$ alkyl, $C_{1-4}$ alkoxy, $CF_3$, $OCF_3$, hydroxy or cyano; heterocyclyl is optionally substituted by $C_{1-4}$ alkyl, $C_{1-4}$ alkoxy($C_{1-4}$ alkyl), oxo or hydroxyl;

or $R^7$ and $R^8$, together with the nitrogen to which the are attached, form a 5- or 6-membered ring optionally comprising a second ring-nitrogen atom, the ring being optionally substituted by oxo, hydroxyl, $C_{1-4}$hydroxyalkyl, $C_{1-4}$ alkyl, $C_{1-4}$ alkoxy($C_{1-4}$ alkyl) or $(CH_2)_pC(O)NR^{12}R^{13}$;

$R^{14}$ and $R^{15}$ are, independently, hydrogen, $C_{1-4}$ alkyl or $C_{1-4}$ hydroxyalkyl; or $R^{14}$ and $R^{15}$ join to form a $C_{3-6}$ cycloalkyl ring;

$R^{10}$, $R^{11}$, $R^{12}$ and $R^{13}$ are, independently, hydrogen or $C_{1-4}$ alkyl;

n and p are, independently, 0, 1, 2, 3 or 4; and

Y is hydrogen, halo, $C_{1-4}$alkyl or $C_{1-4}$haloalkyl;

or a pharmaceutically acceptable salt thereof.

In one embodiment the present invention provides a compound of formula Ib wherein:

A is $C_{1-4}$alkyl, $C_{1-4}$alkoxy or $C_{1-4}$haloalkyl;

$R^3$ is $C_{5-10}$heteroaryl;

W is phenyl substituted by —C(O)NR$^7$R$^8$;

$R^7$ is hydrogen or $C_{1-4}$alkyl;

$R^8$ is selected from hydrogen, $C_{1-6}$alkyl (optionally substituted by one or two groups selected from hydroxyl, $C_{5-10}$aryl and $C_{5-10}$heteroaryl), $C_{3-7}$ cycloalkyl, and $C_{5-10}$heterocyclyl (optionally substituted by one or two groups selected from hydroxyl and oxo);

or a pharmaceutically acceptable salt thereof.

In a further embodiment the present invention provides a compound of formula Ib wherein:

A is $C_{1-2}$haloalkyl;

$R^3$ is $C_{5-10}$heteroaryl;

W is phenyl substituted by —C(O)NR$^7$R$^8$ $R^7$ is hydrogen;

$R^8$ is selected from $C_{1-4}$alkyl (optionally substituted by hydroxyl, $C_{5-6}$aryl and $C_{5-6}$heteroaryl), $C_{5-6}$cycloalkyl (optionally substituted by hydroxyl), and $C_{5-6}$heterocyclyl (optionally substituted by oxo);

or a pharmaceutically acceptable salt thereof.

In another embodiment the present invention provides a compound of formula Ib wherein:

A is $C_{1-2}$-fluoroalkyl;

$R^3$ is benzodioxinyl;

W is phenyl substituted by —C(O)NR$^7$R$^8$;

$R^7$ is hydrogen;

$R^8$ is selected from methyl, ethyl, propyl or butyl (substituted by one or two groups selected from hydroxyl, phenyl and pyridinyl), cyclopentyl, hydroxycyclopentyl, and oxidotetrahydrothiophenyl, dioxidotetrahydrothiophenyl, tetrahydrofuranyl or oxotetrahydrofuranyl;

or a pharmaceutically acceptable salt thereof.

In a further embodiment the present invention provides a compound of formula Ia or Ib wherein A is fluoromethyl, difluoromethyl, trifluoromethyl, fluoroethyl, difluoroethyl, trifluoroethyl, fluoropropyl, difluoropropyl or trifluoropropyl. In one embodiments A is difluoroethyl.

In another embodiment the present invention provides a compound of formula Ia wherein R$^1$ is methyl or ethyl. In one embodiment R$^1$ is methyl.

In one embodiment the present invention provides a compound of formula Ia wherein X is O and Y is hydrogen.

In yet another embodiment the present invention provides a compound of formula Ia or Ib wherein A is difluoroethyl, R$^1$ is methyl, R$^3$ is benzodioxinyl, X is O, Y is hydrogen, W is phenyl substituted by —C(O)NR$^7$R$^8$, R$^7$ is hydrogen and R$^8$ is selected from $C_{1-4}$alkyl (optionally substituted by one or two groups selected from hydroxyl, $C_{5-6}$aryl and $C_{5-6}$heteroaryl), $C_{5-6}$cycloalkyl (optionally substituted by hydroxyl), and $C_{5-6}$heterocyclyl (optionally substituted by oxo).

or a pharmaceutically acceptable salt thereof.

In one embodiment the present invention provides a compound of formula Ia or Ib wherein A is difluoroethyl, R$^1$ is methyl, R$^3$ is benzodioxinyl, X is O, Y is hydrogen, W is phenyl substituted by —C(O)NR$^7$R$^8$, R$^7$ is hydrogen and R$^8$ is selected from $C_{1-4}$alkyl (optionally substituted by one or two groups selected from hydroxyl, $C_{5-6}$aryl and $C_{5-6}$heteroaryl), $C_{5-6}$cycloalkyl, and $C_{5-6}$heterocyclyl (optionally substituted by oxo).

or a pharmaceutically acceptable salt thereof.

In yet a further embodiment the present invention provides a compound of formula Ia or Ib wherein A is difluoroethyl, R$^1$ is methyl, R$^3$ is benzodioxinyl, X is O, Y is hydrogen, W is phenyl substituted by —C(O)NR$^7$R$^8$, R$^7$ is hydrogen and R$^8$ is selected from to methyl or butyl (substituted by one or two groups selected from hydroxyl, phenyl and pyridinyl), cyclypentyl, hydroxycyclopentyl, oxidotetrahydrothiophenyl, dioxidotetrahydrothiophenyl, tetrahydrofuranyl and oxotetrahydrofuranyl, or a pharmaceutically acceptable salt thereof.

In one embodiment R$^8$ is selected from methyl substituted by phenyl.

In another embodiment R$^8$ is methyl substituted by pyridinyl.

In one embodiment R$^8$ is methyl substituted by pyridin-3-yl or pyridin-4-yl.

In one embodiment R$^8$ is butyl substituted by hydroxyl.

In another embodiment R$^8$ is cyclopentyl.

In a further embodiment R$^8$ is hydroxycyclopentyl.

In one embodiment R$^8$ is oxidotetrahydrothiophenyl.

In another embodiment R$^8$ is dioxidotetrahydrothiophenyl.

In a further embodiment R$^8$ is tetrahydrofuranyl.

In one embodiment R$^8$ is oxotetrahydrofuranyl.

In one embodiment R$^8$ is selected from any one of dioxidotetrahydrothiophen-3-yl], oxidotetrahydrothiophen-3-yl], tetrahydrofuran-3-yl, oxotetrahydrofuran-3-yl], cyclopentyl, hydroxycyclopentyl], hydroxybutyl, pyridin-4-ylmethyl, pyridin-3-ylmethyl, phenylmethyl.

In one embodiment the present invention provides a compound of formula Ia or Ib wherein A is difluoroethyl, R$^1$ is methyl, R$^3$ is benzodioxinyl, X is O, Y is hydrogen, W is phenyl substituted by —C(O)NR$^7$R$^8$, R$^7$ is hydrogen and R$^8$ is dioxidotetrahydrothiophenyl.

In another embodiment the present invention provides a compound of formula Ia or Ib wherein A is difluoroethyl, R$^1$ is methyl, R$^3$ is benzodioxinyl, X is O, Y is hydrogen, W is phenyl substituted by —C(O)NR$^7$R$^8$, R$^7$ is hydrogen and R$^8$ is cyclopentyl.

In yet another embodiment the present invention provides a compound of formula Ia or Ib wherein A is difluoroethyl, R$^1$ is methyl, R$^3$ is benzodioxinyl, X is O, Y is hydrogen, W is phenyl substituted by —C(O)NR$^7$R$^8$, R$^7$ is hydrogen and R$^8$ is pyridinyl.

In a further embodiment the present invention provides a compound of formula Ia or Ib wherein A is difluoroethyl, R$^1$ is methyl, R$^3$ is benzodioxinyl, X is O, Y is hydrogen, W is phenyl substituted by —C(O)NR$^7$R$^8$, R$^7$ is hydrogen and R$^8$ is hydroxycyclopentyl.

In one embodiment R³ is 2,3-dihydro-1,4-benzodioxin-6-yl) or 4H-1,3-benzodioxin-7-yl and the other substituents are selected from any combination of substituents as defined above.

For the avoidance of doubt, the present invention relates to any one compound falling within the scope of compounds of formula Ia or Ib.

One embodiment provides compounds selected from:

3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3S)-1,1-dioxidotetrahydrothiophen-3-yl]benzamide (E1), 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3R)-1,1-dioxidotetrahydrothiophen-3-yl]benzamide, 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3RS)-1,1-dioxidotetrahydrothiophen-3-yl]benzamide, 3-(5-{[2-[(2,2-difluoropropanoyl)amino]-1-(2,3-dihydro-1,4-benzodioxin-6-yl)propyl]oxy}-1H-indazol-1-yl)-N-[1,1-dioxidotetrahydrothiophen-3-yl]benzamide, 3-[5-({(1R,2S)-1-(4H-1,3-Benzodioxin-7-yl)-2-[(2,2-difluoropropanoyl)amino]propyl}oxy)-1H-indazol-1-yl]-N-[(3R)-1,1-dioxidotetrahydrothiophen-3-yl]benzamide, 3-[5-({(1R,2S)-1-(4H-1,3-benzodioxin-7-yl)-2-[(2,2-difluoropropanoyl)amino]propyl}oxy)-1H-indazol-1-yl]-N-[(3S)-1,1-dioxidotetrahydrothiophen-3-yl]benzamide, 3-[5-({(1R,2S)-1-(4H-1,3-benzodioxin-7-yl)-2-[(2,2-difluoropropanoyl)amino]propyl}oxy)-1H-indazol-1-yl]-N-[(3RS)-1,1-dioxidotetrahydrothiophen-3-yl]benzamide, 3-[5-({1-(4H-1,3-benzodioxin-7-yl)-2-[(2,2-difluoropropanoyl)amino]propyl}oxy)-1H-indazol-1-yl]-N-[1,1-dioxidotetrahydrothiophen-3-yl]benzamide, 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3S)-tetrahydrofuran-3-yl]benzamide, 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3R)-tetrahydrofuran-3-yl]benzamide, 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3RS)-tetrahydrofuran-3-yl]benzamide, 3-(5-{[2-[(2,2-difluoropropanoyl)amino]-1-(2,3-dihydro-1,4-benzodioxin-6-yl)propyl]oxy}1H-indazol-1-yl)-N-[tetrahydrofuran-3-yl]benzamide, 3-[5-({(1R,2S)-1-(4H-1,3-Benzodioxin-7-yl)-2-[(2,2-difluoropropanoyl)amino]propyl}oxy)-1H-indazol-1-yl]-N-[(3S)-tetrahydrofuran-3-yl]benzamide, 3-[5-({(1R,2S)-1-(4H-1,3-Benzodioxin-7-yl)-2-[(2,2-difluoropropanoyl)amino]propyl}oxy)-1H-indazol-1-yl]-N-[(3R)-tetrahydrofuran-3-yl]benzamide, 3-[5-({(1R,2S)-1-(4H-1,3-Benzodioxin-7-yl)-2-[(2,2-difluoropropanoyl)amino]propyl}oxy)-1H-indazol-1-yl]-N-[(3RS)-tetrahydrofuran-3-yl]benzamide, 3-[5-({1-(4H-1,3-Benzodioxin-7-yl)-2-[(2,2-difluoropropanoyl)amino]propyl}oxy)-1H-indazol-1-yl]-N-[tetrahydrofuran-3-yl]benzamide, N-cyclopentyl-3-(5-{[(1R,2S)-2-[(2,2-difluoropropanoyl)amino]-1-(2,3-dihydro-1,4-benzodioxin-6-yl)propyl]oxy}-1H-indazol-1-yl)benzamide, N-cyclopentyl-3-(5-{[2-[(2,2-difluoropropanoyl)amino]-1-(2,3-dihydro-1,4-benzodioxin-6-yl)propyl]oxy}-1H-indazol-1-yl)benzamide, 3-[5-({(1R,2S)-1-(4H-1,3-benzodioxin-7-yl)-2-[(2,2-difluoropropanoyl)amino]propyl}oxy)-1H-indazol-1-yl]-N-cyclopentylbenzamide, 3-[5-({1-(4H-1,3-benzodioxin-7-yl)-2-[(2,2-difluoropropanoyl)amino]propyl}oxy)-1H-indazol-1-yl]-N-cyclopentylbenzamide, 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(1R,2S)-2-hydroxycyclopentyl]benzamide, 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(1R)-2-hydroxycyclopentyl]benzamide, 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(2S)-2-hydroxycyclopentyl]benzamide, 3-(5-{[2-[(2,2-difluoropropanoyl)amino]-1-(2,3-dihydro-1,4-benzodioxin-6-yl)propyl]oxy}-1H-indazol-1-yl)-N-[2-hydroxycyclopentyl]benzamide, 3-[5-({(1R,2S)-1-(4H-1,3-benzodioxin-7-yl)-2-[(2,2-difluoropropanoyl)amino]propyl}oxy)-1H-indazol-1-yl]-N-[(1R,2S)-2-hydroxycyclopentyl]benzamide, 3-[5-({(1R,2S)-1-(4H-1,3-benzodioxin-7-yl)-2-[(2,2-difluoropropanoyl)amino]propyl}oxy)-1H-indazol-1-yl]-N-[(1S,2R)-2-hydroxycyclopentyl]benzamide, 3-[5-({(1R,2S)-1-(4H-1,3-benzodioxin-7-yl)-2-[(2,2-difluoropropanoyl)amino]propyl}oxy)-1H-indazol-1-yl]-N-[(1S,2S)-2-hydroxycyclopentyl]benzamide, 3-[5-({(1R,2S)-1-(4H-1,3-benzodioxin-7-yl)-2-[(2,2-difluoropropanoyl)amino]propyl}oxy)-1H-indazol-1-yl]-N-[(1R,2R)-2-hydroxycyclopentyl]benzamide, 3-[5-({1-(4H-1,3-benzodioxin-7-yl)-2-[(2,2-difluoropropanoyl)amino]propyl}oxy)-1H-indazol-1-yl]-N-[2-hydroxycyclopentyl]benzamide, 3-[5-({(1R,2S)-1-(4H-1,3-benzodioxin-7-yl)-2-[(2,2-difluoropropanoyl)amino]propyl}oxy)-1H-indazol-1-yl]-N-[(2R)-2-hydroxybutyl]benzamide, 3-[5-({(1R,2S)-1-(4H-1,3-benzodioxin-7-yl)-2-[(2,2-difluoropropanoyl)amino]propyl}oxy)-1H-indazol-1-yl]-N-[(2S)-2-hydroxybutyl]benzamide, 3-[5-({1-(4H-1,3-benzodioxin-7-yl)-2-[(2,2-difluoropropanoyl)amino]propyl}oxy)-1H-indazol-1-yl]-N-[2-hydroxybutyl]benzamide, 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-(pyridin-3-ylmethyl)benzamide, 3-(5-{[2-[(2,2-difluoropropanoyl)amino]-1-(2,3-dihydro-1,4-benzodioxin-6-yl)propyl]oxy}-1H-indazol-1-yl)-N-(pyridin-3-ylmethyl)benzamide, 3-[5-({(1R,2S)-1-(4H-1,3-benzodioxin-7-yl)-2-[(2,2-difluoropropanoyl)amino]propyl}oxy)-1H-indazol-1-yl]-N-(pyridin-3-ylmethyl)benzamide, 3-[5-({1-(4H-1,3-benzodioxin-7-yl)-2-[(2,2-difluoropropanoyl)amino]propyl}oxy)-1H-indazol-1-yl]-N-(pyridin-3-ylmethyl)benzamide, 3-[5-({(1R,2S)-1-(4H-1,3-benzodioxin-7-yl)-2-[(2,2-difluoropropanoyl)amino]propyl}oxy)-1H-indazol-1-yl]-N-[(3S)-1-oxidotetrahydrothiophen-3-yl]benzamide (Isomer 1), 3-[5-({(1R,2S)-1-(4H-1,3-benzodioxin-7-yl)-2-[(2,2-difluoropropanoyl)amino]propyl}oxy)-1H-indazol-1-yl]-N-[(3R)-1-oxidotetrahydrothiophen-3-yl]benzamide (Isomer 2), 3-[5-({(1R,2S)-1-(4H-1,3-benzodioxin-7-yl)-2-[(2,2-difluoropropanoyl)amino]propyl}oxy)-1H-indazol-1-yl]-N-[(3RS)-1-oxidotetrahydrothiophen-3-yl]benzamide, 3-[5-({1-(4H-1,3-benzodioxin-7-yl)-2-[(2,2-difluoropropanoyl)amino]propyl}oxy)-1H-indazol-1-yl]-N-[1-oxidotetrahydrothiophen-3-yl]benzamide, 3-[5-({(1R,2S)-1-(4H-1,3-benzodioxin-7-yl)-2-[(2,2-difluoropropanoyl)amino]propyl}oxy)-1H-indazol-1-yl]-N-benzylbenzamide, 3-[5-({1-(4H-1,3-benzodioxin-7-yl)-2-[(2,2-difluoropropanoyl)amino]propyl}oxy)-1H-indazol-1-yl]-N-benzylbenzamide, 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3R)-2-oxotetrahydrofuran-3-yl]benzamide, 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3S)-2-oxotetrahydrofuran-3-yl]benzamide, 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3SR)-2-oxotetrahydrofuran-3-yl]benzamide, and 3-(5-{[2-[(2,2-difluoropropanoyl)amino]-1-(2,3-dihydro-1,4-benzodioxin-6-yl)propyl]oxy}-1H-indazol-1-yl)-N-[2-oxotetrahydrofuran-3-yl]benzamide, or a pharmaceutically acceptable salt thereof.

Another embodiment provides compounds selected from:

3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3S)-1,1-dioxidotetrahydrothiophen-3-yl]benzamide (E1), 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3R)-1,1-dioxidotetrahydrothiophen-3-yl]benzamide, 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3RS)-1,1-dioxidotetrahydrothiophen-3-yl]benzamide, 3-[5-({(1R,2S)-1-(4H-1,3-Benzodioxin-7-yl)-2-[(2,2-difluoropropanoyl)amino]propyl}oxy)-1H-indazol-1-yl]-N-[(3R)-1,1-dioxidotetrahydrothiophen-3-yl]benzamide, 3-[5-({(1R,2S)-1-(4H-1,3-benzodioxin-7-yl)-2-[(2,2-difluoropropanoyl)amino]propyl}oxy)-1H-indazol-1-yl]-N-[(3S)-1,1-dioxidotetrahydrothiophen-3-yl]benzamide, 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-(3S)-tetrahydrofuran-3-yl]benzamide, 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3R)-tetrahydrofuran-3-yl]benzamide, 3-[5-({(1R,2S)-1-(4H-1,3-Benzodioxin-7-yl)-2-[(2,2-difluoropropanoyl)amino]propyl}oxy)-1H-indazol-1-yl]-N-[(3S)-tetrahydrofuran-3-yl]benzamide, N-cyclopentyl-3-(5-{[(1R,2S)-2-[(2,2-difluoropropanoyl)amino]-1-(2,3-dihydro-1,4-benzodioxin-6-yl)propyl]oxy}-1H-indazol-1-yl)benzamide, 3-[5-({(1R,2S)-1-(4H-1,3-benzodioxin-7-yl)-2-[(2,2-difluoropropanoyl)amino]propyl}oxy)-1H-indazol-1-yl]-N-cyclopentylbenzamide, 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(1R,2S)-2-hydroxycyclopentyl]benzamide, 3-[5-({(1R,2S)-1-(4H-1,3-benzodioxin-7-yl)-2-[(2,2-difluoropropanoyl)amino]propyl}oxy)-1H-indazol-1-yl]-N-[(1R,2S)-2-hydroxycyclopentyl]benzamide, 3-[5-({(1R,2S)-1-(4H-1,3-benzodioxin-7-yl)-2-[(2,2-difluoropropanoyl)amino]propyl}oxy)-1H-indazol-1-yl]-N-[(1S,2S)-2-hydroxycyclopentyl]benzamide, 3-[5-({(1R,2S)-1-(4H-1,3-benzodioxin-7-yl)-2-[(2,2-difluoropropanoyl)amino]propyl}oxy)-1H-indazol-1-yl]-N-[(2R)-2-hydroxybutyl]benzamide, 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-(pyridin-3-ylmethyl)benzamide, 3-[5-({(1R,2S)-1-(4H-1,3-benzodioxin-7-yl)-2-[(2,2-difluoropropanoyl)amino]propyl}oxy)-1H-indazol-1-yl]-N-(pyridin-3-ylmethyl)benzamide, 3-[5-({(1R,2S)-1-(4H-1,3-benzodioxin-7-yl)-2-[(2,2-difluoropropanoyl)amino]propyl}oxy)-1H-indazol-1-yl]-N-[(3S)-1-oxidotetrahydrothiophen-3-yl]benzamide (Isomer 1), 3-[5-({(1R,2S)-1-(4H-1,3-benzodioxin-7-yl)-2-[(2,2-difluoropropanoyl)amino]propyl}oxy)-1H-indazol-1-yl]-N-[(3S)-1-oxidotetrahydrothiophen-3-yl]benzamide (Isomer 2), 3-[5-({(1R,2S)-1-(4H-1,3-benzodioxin-7-yl)-2-[(2,2-difluoropropanoyl)amino]propyl}oxy)-1H-indazol-1-yl]-N-benzylbenzamide, and 3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3R)-2-oxotetrahydrofuran-3-yl]benzamide, or a pharmaceutically acceptable salt thereof.

For the avoidance of doubt, the present invention relates to any one specific compound mentioned in the list of compounds.

For the avoidance of doubt it is to be understood that where in this specification a group is qualified by 'hereinbefore defined', 'defined hereinbefore' or 'defined above' the said group encompasses the first occurring and broadest definition as well as each and all of the other definitions for that group.

For the avoidance of doubt it is to be understood that in this specification '$C_{1-6}$' means a carbon group having 1, 2, 3, 4, 5 or 6 carbon atoms.

In this specification, unless stated otherwise, the term "alkyl" includes both straight and branched chain alkyl groups and may be, but are not limited to methyl, ethyl, n-propyl, i-propyl, n-butyl, i-butyl, s-butyl, t-butyl, n-pentyl, i-pentyl, neo-pentyl, n-hexyl or i-hexyl. The term $C_{1-4}$ alkyl having 1 to 4 carbon atoms and may be but are not limited to methyl, ethyl, n-propyl, i-propyl or t-butyl. The term "$C_0$" in $C_{0-4}$ alkyl refers to a situation where no carbon atom is present.

The term 'alkyl' and 'alkylenyl' refers to a straight or branched chain alkyl group linking two other atoms. It is, for example, $CH_2$ (methyl), $CH_2CH_2$ (ethyl), $CH_2CH_2CH_2$ or $CH_2CH_3CH_2$— (propyl) etc.

The term "alkoxy", unless stated otherwise, refers to radicals of the general formula —O—R, wherein R is selected from a hydrocarbon radical. The term "alkoxy" may include, but is not limited to methoxy, ethoxy, propoxy, isopropoxy, butoxy, t-butoxy, iso-butoxy, cyclopropylmethoxy, allyloxy or propargyloxy.

In this specification, unless stated otherwise, the term "cycloalkyl" refers to an optionally substituted, partially or completely saturated monocyclic, bicyclic or bridged hydrocarbon ring system. The term "$C_{3-7}$cycloalkyl" may be, but is not limited to cyclopropyl, cyclobutyl, cyclopentyl or cyclohexyl as well as hydroxycyclopentyl.

In this specification, unless stated otherwise, the term "heterocycloalkyl" or "heterocyclyl" refers to an optionally substituted, partially or completely saturated monocyclic, bicyclic or bridged hydrocarbon ring system having one or more heteroatoms independently selected from O, N or S. The term "$C_{3-7}$heterocycloalkyl" may be, but is not limited to pyrrolidinyl, piperidinyl, piperazinyl, tetrahydrothiophenyl, oxidotetrahydrothiophenyl, dioxidotetrahydrothiophenyl tetrahydrofuranyl or oxotetrahydrofuranyl.

In this specification, unless stated otherwise, the term "a 5- or 6-membered ring optionally comprising a second ring-nitrogen atom" refers to heterocycloalkyl as defined above and may be, but is not limited to pyrrolidinyl, prolinamide or piperazinyl.

In this specification, unless stated otherwise, the terms "halo" and "halogen" may be fluorine (fluoro), iodine (iodo), chlorine (chloro) or bromine (bromo).

In this specification, unless stated otherwise, the term "haloalkyl" means an alkyl group as defined above, which is substituted with halo as defined above. The term "$C_{1-6}$haloalkyl" may include, but is not limited to fluoromethyl, difluoromethyl, trifluoromethyl, fluoroethyl, difluoroethyl, trifluoroethyl, fluoropropyl, difluoropropyl or trifluoropropyl, chloromethyl, dichloromethyl, trichloromethyl or fluorochloromethyl.

The term "$C_{1-3}$haloalkylO" or "$C_{1-3}$haloalkoxy" may include, but is not limited to fluoromethoxy, difluoromethoxy, trifluoromethoxy, fluoroethoxy or difluoroethoxy.

In this specification, unless stated otherwise, the term "thioalkyl" means an alkyl group as defined above, which is substituted with sulphur atom. The term "$C_{1-6}$thioalkyl" may include, but is not limited to methylsulfanyl, ethylsulfanyl or propylsulfanyl.

The term "cycloalkylthio" means a sulphur atom substituted with a cycloalkyl as defined above such as for instance cyclopropylsulfanyl.

The term "$C_{1-4}$alkylthioalkyl" means a alkyl group with a sulphur atom between the carbon atoms. The term "$C_{1-4}$alkylthioC$_{1-4}$alkyl" may include, but is not limited to ethylsulfanylmethyl.

In this specification, unless stated otherwise, the term "$C_{5-10}$aryl" or aryl refers to an aromatic or partial aromatic group having 5 to 10 carbon atoms such as for example, phenyl or naphthyl. The term "$C_{5-10}$aryloxy" or "$C_{5-10}$arylO" refers to for example phenoxy.

In this specification, unless stated otherwise, the term "$C_{5-10}$heteroaryl" or heteroaryl refers to a mono- or bicyclic aromatic or partially aromatic ring with 5 to 10 atoms and containing one or more heteroatoms independently selected from nitrogen, oxygen or sulphur. Heteroaryl is, for example, oxazolyl, isoxazolyl, 1,2,4-oxadiazolyl, furyl, thienyl, thiophenyl, pyrrolyl, pyrazolyl, imidazolyl, 1,2,4-triazolyl, pyridinyl, pyrimidinyl, indolyl, indazolyl, benzofuryl, benzothienyl, benzodioxinyl, dioxabicyclodecatrienyl, quinolinyl or isoquinolinyl.

When aryl (for example phenyl) or heteroaryl is substituted by $(CH_2)_tOC_{1-4}$alkylenylO$(CH_2)_v$ or $(CH_2)_tO(CH_2)_v$; wherein t and v are, independently, 0, 1, 2 or 3, but t and v are not both 0; these substituents can be, for example, $CH_2OCH_2O$, $OCH_2O$, $OCH_2CH_2O$ or $OCH_2CH_2$ linking adjacent carbons on the aryl or heteroaryl ring.

For the avoidance of doubt a group $R^3$ defined as $C_{5-10}$aryl e.g. phenyl, substituted with a group $C_{1-2}$alkylS(O)$_k$ includes a phenyl substituted with methylsulphonyl group.

It will be appreciated that throughout the specification, the number and nature of substituents on rings in the compounds of the invention will be selected so as to avoid sterically undesirable combinations.

Compounds of the present invention have been named with the aid of computer software (ACDLabs 10.06/Name(IUPAC)).

Compounds of the invention may include an asymmetric centre and be chiral in nature. Where the compound is chiral, it may be in the form of a single stereoisomer, such as a enantiomer, or it may be in the form of mixtures of these stereoisomers in any proportions, including racemic mixtures. Therefore, all enantiomers, diastereomers, racemates and mixtures thereof are included within the scope of the invention. The various optical isomers may be isolated by separation of a racemic mixture of the compounds using conventional techniques, for example, fractional crystallisation, or HPLC. Alternatively the optical isomers may be obtained by asymmetric synthesis, or by synthesis from optically active starting materials.

Compounds of the invention may be converted to a pharmaceutically acceptable salt thereof, such as an acid addition salt such as a hydrochloride, hydrobromide, phosphate, sulfphate, acetate, ascorbate, benzoate, fumarate, hemifumarate, furoate, succinate, maleate, tartrate, citrate, oxalate, xinafoate, methanesulphonate, p-toluenesulphonate, benzenesulphonate, ethanesulphonate, 2-naphthalenesulfonate, mesytilenesulfonate, nitric acid, 1,5-naphthalene-disulphonate, p-xylenesulphonate, aspartate or glutamate. They may also include basic addition salts such as an alkali metal salt for example sodium or potassium salts, an alkaline earth metal salt for example calcium or magnesium salts, a transition metal salt such as a zinc salt, an organic amine salt for example a salt of triethylamine, diethylamine, morpholine, N-methylpiperidine, N-ethylpiperidine, piperazine, procaine, dibenzylamine, N,N-dibenzylethylamine, choline or 2-aminoethanol or amino acids for example lysine or arginine.

The compounds of the invention, or a pharmaceutically acceptable salt thereof, may exist in solvated, for example hydrated, as well as unsolvated forms, or as cocrystals and the present invention encompasses all such forms.

Process

The compounds of the invention can be prepared using or adapting methods disclosed in the art, or by using or adapting the method disclosed in the Example below. Starting materials for the preparative methods are either commercially available or can be prepared by using or adapting literature methods.

A process for the synthesis of a compound of formula Ia or Ib can comprise using an acid/amine coupling reaction disclosed in WO 2007/122165, WO 2008/043788 or WO 2008/076048. For example using as an intermediate a compound of formula (Ic) or (Id):

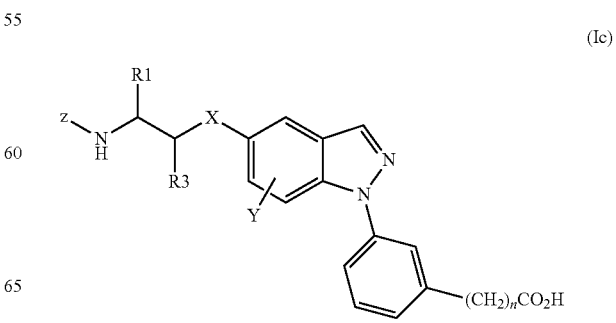

(Ic)

-continued (Id)
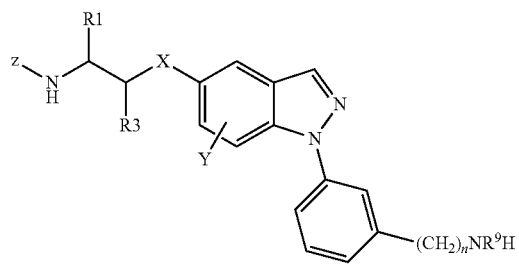

wherein $R^1$, $R^3$, X and Y are defined as above, and Z is A-C(O) or A-S(O)$_2$. A compound of the invention can be prepared if an acid of formula (Ic) is reacted with an amine of formula HNR$^7$R$^8$ or HNR$^9$(CR$^{14}$R$^{15}$)C(O)NR$^7$R$^8$. Alternatively, a compound of the invention can be prepared by reaction of an amine of formula (Id) with an acid as defined by HOC(O)R$^8$. The compounds of formula (Ic) and (Id) can be synthesised from protected precursors such as alkylesters for the synthesis of (Ic), or from an N-protected precursor of NR$^9$H such as NR$^9$BOC or N$_3$ for the preparation of (Id).

One embodiment relates to a process for the preparation of compounds of formula Ia or Ib by coupling a compound of formula (II):

(II)
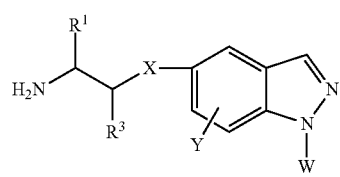

with acylation reagents of formula (IIIa), (IIIb) or (IIIc)

(IIIa)
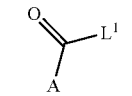

(IIIb)
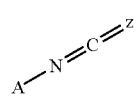

(IIIc)

wherein $R^1$, $R^3$, A, X and Y are defined above, W is as defined above or can be a group that can be converted into W as defined above, and L$^1$ is a leaving group {such as halogen (for example chloro) or, when L$^1$=OH, a leaving group generated by reaction of a coupling reagent (such as HATU with a carboxylic acid)}. The reaction may be performed in a suitable solvent (such as pyridine, THF or DMF), in the presence of a suitable base (such as a tri(C$_{1-6}$ alkyl)amine, for example diisopropylethylamine, or pyridine) and at a suitable temperature (such as −10° to 50° C.).

A compound of formula (II) can be prepared according to step a, b or c.

a) A compound of formula (II) can be prepared by coupling a compound of formula (IV)

(IV)
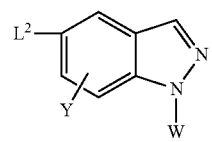

wherein W and Y are as defined above and L$^2$ is a leaving group (such as halogen or triflate) with a compound of formula (V)

(V)
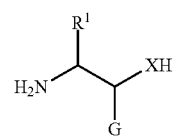

wherein $R^1$ and X are defined above and G corresponds to $R^3$ or a protected precurser to $R^3$. The reaction can be performed in a suitable solvent (such as an aromatic solvent, for example toluene) or a polar, aprotic solvent, such as DMF or butyronitril, in the presence of a suitable base (such as a alkali metal alkoxide (for example sodium tert-butoxide) or, cesium carbonate, such as mediated by a suitable metal catalyst such as Copper(I) iodide at a suitable temperature (for example in the range 80° to 120° C.).

Or, b) A compound of formula (II) can be prepared by reacting a compound of formula (VII)

(VII)
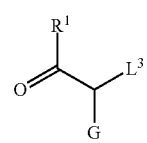

with a compound of formula (VIII)

(VIII)
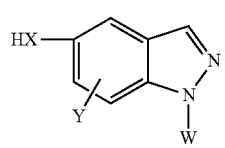

wherein $R^1$, X, W and Y are defined above, G corresponds to $R^3$ or a protected precurser to $R^3$, and L$^3$ is a leaving group (such as halogen, mesylate or tosylate). The reaction can be performed in a suitable solvent (such as DCM, DMF or acetonitrile), in the presence of a suitable base (such as an alkali metal carbonate, for example cesium carbonate or potassium carbonate) at a suitable temperature (for example in the range −10 to 50° C.), followed by a subsequent reductive amination step using or adopting literature methods.

Or, c) a compound of formula (II) may be prepared by reacting a compound of formula (VIII) with a compound of formula (IX)

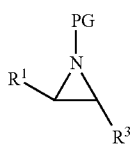

wherein $R^1$ and $R^3$ are as defined above, and PG is a suitable protecting group such as BOC, mesyl or tosyl or related carbonyl- or sulfonyl residues. The reaction can be performed in a suitable solvent such as DCM or toluene in the presence of a suitable base such as NaH or KOtBu, followed by a deprotection step using or adopting literature methods.

As a specific case of a compound of formula (V), a compound of formula (X) might be used to prepare a compound of formula (II)

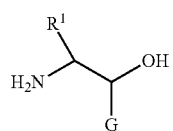

wherein R' and G are defined as in compounds of formula (V).

Compounds of formula (X) may be prepared by reacting a nucleophile G-M with a carbonyl compound of formula (XI) followed reduction and subsequent deprotection of the intermediate of formula (XII)

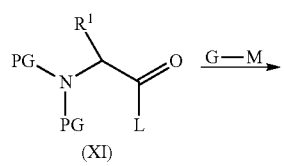

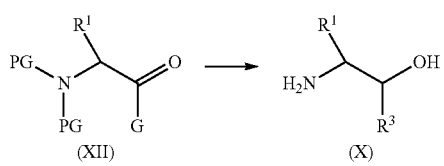

wherein $R^1$, $R^3$, G and PG are as defined above, and L is a leaving group (such as alkoxy, methoxy(methyl)amino), M is a metal such as $L^1$ or Mg-halide. The addition of the nucleophile may be performed in a suitable aprotic solvent such as THF at moderate temperature between −10 and 50° C. The following reduction and deprotection steps might be carried out by using or adopting literature methods.

Alternatively, compounds of formula (X) may be prepared by a reaction of a nuceophile G-M with an aldehyde of formula (XIII) and a subsequent deprotection.

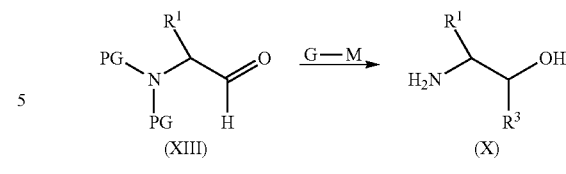

wherein $R^1$, $R^3$, G and PG are as defined above, and M is a metal such as an alkali metal (e.g. Li) or Mg-halide. The reaction may be performed by following disclosed protocols for addition of carbanions to aldehydes.

Another way to prepare a compound of formula (X) is the reaction of a nitroalkyle of formula (XIV) with an aldehyde of formula (XV), followed by reduction of the nitro function

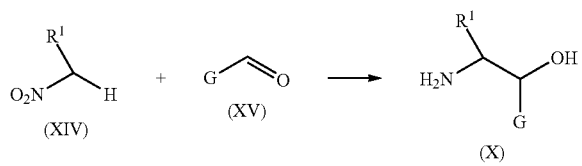

wherein $R^1$, $R^3$ and G are as defined above. Both steps may be carried out by following or adopting literature methods.

Medical Use

Because of their ability to bind to the glucocorticoid receptor the compounds of the is invention are useful as anti-inflammatory agents, and can also display antiallergic, immunosuppressive and anti-proliferative actions. Thus, a compound of formula Ia or Ib, or a pharmaceutically acceptable salt thereof can be used as a medicament for the treatment or prophylaxis of one or more of the following pathologic conditions (disease states) in a mammal (such as a human):

(i) Lung diseases, which coincide with inflammatory, allergic and/or proliferative processes:

chronically obstructive lung diseases of any origin, mainly bronchial asthma, chronic obstructive pulmonary disease bronchitis of different origins Adult respiratory distress syndrome (ARDS), acute respiratory distress syndrome Bronchiectases all forms of restrictive lung diseases, mainly allergic alveolitis all forms of pulmonary edema, mainly toxic pulmonary edema sarcoidoses and granulomatoses, such as Boeck's disease (ii) Rheumatic diseases/auto-immune diseases/degenerative joint diseases, which coincide with inflammatory, allergic and/or proliferative processes:

all forms of rheumatic diseases, for example rheumatoid arthritis, acute rheumatic fever, polymyalgia rheumatica, collagenoses, Behçet's disease reactive arthritis inflammatory soft-tissue diseases of other origins arthritic symptoms in degenerative joint diseases (arthroses)

traumatic arthritides collagen diseases of other origins, for example systemic lupus erythematodes, discoid lupus erythematosus, sclerodermia, polymyositis, dermatomyositis, polyarteritis nodosa, temporal arteritis Sjögren's syndrome, Still syndrome, Felty's syndrome Vitiligo Soft-tissue rheumatism (iii) Allergies, which coincide with inflammatory, allergic and/or proliferative processes:
All forms of allergic reactions, for example Quincke's edema, insect bites, allergic reactions to pharmaceutical agents, blood derivatives, contrast media, etc., anaphylactic shock, urticaria, contact dermatitis (e.g. allergic and irritative), allergic vascular diseases
Allergic vasculitis
inflammatory vasculitis
(iv) Vascular inflammations (vasculitides)
Panarteritis nodosa, temporal arteritis, erythema nodosum
Polyarteris nodosa
Wegner's granulomatosis
Giant-cell arteritis
(v) Dermatological diseases, which coincide with inflammatory, allergic and/or proliferative processes:
atopic dermatitis (mainly in children)
exfoliative dermatitis,
psoriasis
erythematous diseases, triggered by different noxae, for example radiation, chemicals, burns, etc.
acid burns
bullous dermatoses, such as, for example, autoimmune pemphigus vulgaris, bullous
pemphigoid
diseases of the lichenoid group itching (for example of allergic origins)
all forms of eczema, such as, for example, atopic eczema or seborrheal eczema rosacea
pemphigus vulgaris
erythema exudativum multiforme
erythema nodosum
balanitis
Pruritis, such as, for example, allergic origin)
Manifestation of vascular diseases
vulvitis
inflammatory hair loss, such as alopecia areata
cutaneous T-cell lymphoma
Rashes of any origin or dermatoses
Psoriasis and parapsoriasis groups
Pityriasis rubra pilaris
(vi) Nephropathies, which coincide with inflammatory, allergic and/or proliferative processes:
nephrotic syndrome
all nephritides, such as, for example, glomerulonephritis
(vii) Liver diseases, which coincide with inflammatory, allergic and/or proliferative processes:
acute liver cell decomposition
acute hepatitis of different origins, for example virally-, toxically- or pharmaceutical agent-induced
chronically aggressive and/or chronically intermittent hepatitis
(viii) Gastrointestinal diseases, which coincide with inflammatory, allergic and/or proliferative processes:
regional enteritis (Crohn's disease)
Gastritis
Reflux esophagitis
ulcerative colitis
gastroenteritis of other origins, for example native sprue
(ix) Proctological diseases, which coincide with inflammatory, allergic and/or proliferative processes:
anal eczema
fissures
haemorrhoids
idiopathic proctitis
(x) Eye diseases, which coincide with inflammatory, allergic and/or proliferative processes:
allergic keratitis, uvenitis iritis
conjunctivitis
blepharitis
optic neuritis
chorioiditis
sympathetic ophthalmia
(xi) Diseases of the ear-nose-throat area, which coincide with inflammatory, allergic and/or proliferative processes:
allergic rhinitis, hay fever
otitis externa, for example caused by contact dermatitis, infection, etc.
otitis media
(xii) Neurological diseases, which coincide with inflammatory, allergic and/or proliferative processes:
cerebral edema, mainly tumor-induced cerebral edema
multiple sclerosis
acute encephalomyelitis
different forms of convulsions, for example infantile nodding spasms
Meningitis
spinal cord injury
Stroke
(xiii) Blood diseases, which coincide with inflammatory, allergic and/or proliferative processes:
acquired haemolytic anemia
thrombocytopenia such as for example idiopathic thrombocytopenia
M. Hodgkins or Non-Hodgkins lymphomas,
thrombocythemias,
erythrocytoses
(xiv) Tumor diseases, which coincide with inflammatory, allergic and/or proliferative processes:
acute lymphatic leukaemia
malignant lymphoma
lymphogranulomatoses
lymphosarcoma
extensive metastases, mainly in breast and prostate cancers
(xv) Endocrine diseases, which coincide with inflammatory, allergic and/or proliferative processes:
endocrine orbitopathy
thyrotoxic crisis
de Quervain's thyroiditis
Hashimoto's thyroiditis
Hyperthyroidism
Basedow's disease
Granulomatous thyroiditis
Lymphadenoid goiter
(xvi) Transplants, which coincide with inflammatory, allergic and/or proliferative processes;
(xvii) Severe shock conditions, which coincide with inflammatory, allergic and/or proliferative processes, for example anaphylactic shock
(xviii) Substitution therapy, which coincides with inflammatory, allergic and/or proliferative processes, with:
innate primary suprarenal insufficiency, for example congenital adrenogenital syndrome acquired primary suprarenal insufficiency, for example Addison's disease, autoimmune adrenalitis, meta-infective, tumors, metastases, etc.
innate secondary suprarenal insufficiency, for example congenital hypopituitarism acquired secondary suprarenal insufficiency, for example meta-infective, tumors, etc.

(xix) Emesis, which coincides with inflammatory, allergic and/or proliferative processes:
for example in combination with a 5-$HT_3$-antagonist in cytostatic-agent-induced vomiting.
(xx) Pains of inflammatory origins, e.g., lumbago Without prejudice to the foregoing, the compounds of the invention can also be used to treat disorders such as: diabetes type I (insulin-dependent diabetes), Guillain-Barré syndrome, restenoses after percutaneous transluminal angioplasty, Alzheimer's disease, acute and chronic pain, arteriosclerosis, reperfusion injury, thermal injury, multiple organ injury secondary to trauma, acute purulent meningitis, necrotizing enterocolitis and syndromes associated with hemodialysis, leukopheresis, granulocyte transfusion, Conies Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, disorders associated with excess catecholamine levels, diastolic and systolic congestive heart failure (CHF), peripheral vascular disease, diabetic nephropathy, cirrhosis with edema and ascites, oesophageal varicies, muscle weakness, increased melanin pigmentation of the skin, weight loss, hypotension, hypoglycemia, Cushing's Syndrome, obesity, glucose intolerance, hyperglycemia, diabetes mellitus, osteoporosis, polyuria, polydipsia, inflammation, autoimmune disorders, tissue rejection associated with organ transplant, malignancies such as leukemias and lymphomas, rheumatic fever, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, hypercalcemia, acute adrenal insufficiency, chronic primary adrenal insufficiency, secondary adrenal insufficiency, congenital adrenal hyperplasia, Little's syndrome, systemic inflammation, inflammatory bowel disease, Wegener's granulomatosis, giant cell arthritis, osteoarthritis, angioneurotic edema, tendonitis, bursitis, autoimmune chronic active hepatitis, hepatitis, cinhosis, panniculitis, inflamed cysts, pyoderma gangrenosum, eosinophilic fasciitis, relapsing polychondritis, sarcoidosis Sweet's disease, type 1 reactive leprosy, capillary hemangiomas, lichen planus, erythema nodosum acne, hirsutism, toxic epidermal necrolysis, erythema multiform, psychoses, cognitive disorders (such as memory disturbances) mood disorders (such as depression and bipolar disorder), anxiety disorders and personality disorders.

As used herein the term "congestive heart failure" (CHF) or 'congestive heart disease" refers to a disease state of the cardiovascular system whereby the heart is unable to efficiently pump an adequate volume of blood to meet the requirements of the body's tissues and organ systems. Typically, CHF is characterized by left ventricular failure (systolic dysfunction) and fluid accumulation in the lungs, with the underlying cause being attributed to one or more heart or cardiovascular disease states including coronary artery disease, myocardial infarction, hypertension, diabetes, valvular heart disease, and cardiomyopathy. The term "diastolic congestive heart failure" refers to a state of CHF characterized by impairment in the ability of the heart to properly relax and fill with blood. Conversely, the term "systolic congestive heart failure" refers to a state of CHF characterized by impairment in the ability of the heart to properly contract and eject blood.

As will be appreciated by one of skill in the art, physiological disorders may present as a "chronic" condition, or an "acute" episode. The term "chronic", as used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of physiological disorders contemplates both acute events and chronic conditions. In an acute event, compound is administered at the onset of symptoms and discontinued when the symptoms disappear.

In another aspect the present invention provides a compound of formula Ia or Ib, or a pharmaceutically acceptable salt thereof, for use in therapy (such as a therapy described above).

In yet another aspect the present invention provides the use of a compound of formula Ia or Ib, or a pharmaceutically acceptable salt thereof, in the manufacture of a medicament for use in the treatment of a glucocorticoid receptor mediated disease state (such as a disease state described above).

In a further aspect the invention provides the use of a compound of formula Ia or Ib, or a pharmaceutically acceptable salt thereof, in the manufacture of a medicament for use in the treatment of an inflammatory condition (such as an arthritic).

In a further aspect the invention provides the use of a compound of formula Ia or Ib, or a pharmaceutically acceptable salt thereof, in the manufacture of a medicament for use in the treatment of a respiratory condition.

In a still further aspect the invention provides the use of a compound of formula Ia or Ib, or a pharmaceutically acceptable salt thereof, in the manufacture of a medicament for use in the treatment of asthma.

In another aspect the invention provides the use of a compound of formula Ia or Ib, or a pharmaceutically acceptable salt thereof, in the manufacture of a medicament for use in the treatment of COPD.

In another aspect the present invention provides a compound of formula Ia or Ib, or a pharmaceutically acceptable salt thereof, for use in treating an inflammatory condition, a respiratory condition, asthma and/or COPD.

The present invention further provides a method of treating a glucocorticoid receptor mediated disease state (such as a disease state described above), an inflammatory condition, a respiratory condition, asthma and/or COPD, in a mammal (such as man), which comprises administering to a mammal in need of such treatment an effective amount of a compound of formula Ia or Ib, or a pharmaceutically acceptable salt thereof.

In the context of the present specification, the term "therapy" and "treatment" also includes prophylaxis and prevention unless there are specific indications to the contrary. The terms "therapeutic" and "therapeutically" should be construed accordingly. In this specification, unless stated otherwise, the terms "inhibitor" and "antagonist" mean a compound that by any means, partly or completely, blocks the transduction pathway leading to the production of a response by the agonist. An agonist may be a full or partial agonist.

The term "disorder", unless stated otherwise, means any condition and disease associated with glucocorticoid receptor activity.

Pharmaceutical Composition

In order to use a compound of formula Ia or Ib, or a pharmaceutically acceptable salt thereof, for the therapeutic treatment of a mammal, said active ingredient is normally formulated in accordance with standard pharmaceutical practice as a pharmaceutical composition.

Therefore another aspect the present invention provides a pharmaceutical composition comprising a compound of formula Ia or Ib, or a pharmaceutically acceptable salt thereof, (active ingredient) and a pharmaceutically acceptable adjuvant, diluent or carrier. One embodiment relates to the use of a pharmaceutical composition comprising a compound of formula Ia or Ib, or a pharmaceutically acceptable salt thereof, for treating a glucocorticoid receptor mediated disease state (such as a disease state described above), an inflammatory condition, asthma and/or COPD.

A further aspect the present invention provides a process for the preparation of said composition comprising mixing the active ingredient with a pharmaceutically acceptable adjuvant, diluent or carrier. Depending on the mode of administration, the pharmaceutical composition can comprise from 0.05 to 99% w (percent by weight), for example from 0.05 to 80% w, such as from 0.10 to 70% w (for example from 0.10 to 50% w), of active ingredient, all percentages by weight being based on total composition.

A pharmaceutical composition of the present invention can be administered in a standard manner for the disease condition that it is desired to treat, for example by topical (such as to the lung and/or airways or to the skin), oral, rectal or parenteral administration. Thus, a compound of formula Ia or Ib, or a pharmaceutically acceptable salt thereof, may be formulated into the form of, for example, an aerosol, a powder (for example dry or dispersible), a tablet, a capsule, a syrup, a granule, an aqueous or oily solution or suspension, an (lipid) emulsion, a suppository, an ointment, a cream, drops, or a sterile injectable aqueous or oily solution or suspension.

A suitable pharmaceutical composition of this invention is one suitable for oral administration in unit dosage form, for example a tablet or capsule containing between 0.1 mg and 10 g of active ingredient.

In another aspect a pharmaceutical composition of the invention is one suitable for intravenous, subcutaneous, intraarticular or intramuscular injection.

In one embodiment a compound of formula Ia or Ib, or a pharmaceutically acceptable salt thereof, is administered orally.

In another embodiment a compound of formula Ia or Ib, or a pharmaceutically acceptable salt thereof, is administered by inhalation.

Buffers, pharmaceutically-acceptable cosolvents such as polyethylene glycol, polypropylene glycol, glycerol or ethanol or complexing agents such as hydroxy-propyl β-cyclodextrin may be used to aid formulation.

The above formulations may be obtained by conventional procedures well known in the pharmaceutical art. Tablets may be enteric coated by conventional means, for example to provide a coating of cellulose acetate phthalate.

The invention further relates to a combination therapy or composition wherein a compound of formula Ia or Ib, or a pharmaceutically acceptable salt thereof, or a pharmaceutical composition comprising a compound of formula Ia or Ib, or a pharmaceutically acceptable salt thereof, is administered concurrently (possibly in the same composition) or sequentially with one or more agents for the treatment of any of the above disease states.

For example, for the treatment of rheumatoid arthritis, osteoarthritis, COPD, asthma or allergic rhinitis a compound of formula Ia or Ib, or a pharmaceutically acceptable salt thereof, can be combined with one or more agents for the treatment of such a condition. Where such a combination is to be administered by inhalation, then the one or more agents is selected from the list comprising:

a PDE4 inhibitor including an inhibitor of the isoform PDE4D;

a selective β.sub2. adrenoceptor agonist such as metaproterenol, isoproterenol, isoprenaline, albuterol, salbutamol, formoterol, salmeterol, terbutaline, orciprenaline, bitolterol mesylate, pirbuterol or indacaterol;

a muscarinic receptor antagonist (for example a M1, M2 or M3 antagonist, such as a selective M3 antagonist) such as ipratropium bromide, tiotropium bromide, oxitropium bromide, pirenzepine or telenzepine;

a modulator of chemokine receptor function (such as a CCR1 receptor antagonist);

an inhibitor of p38 kinase function;

an inhibitor of matrix metalloproteases, such as targeting MMP-2, -9 or MMP-12; or, an inhibitor of neutrophil serine proteases, such as neutrophil elastase or proteinase 3.

In another embodiment of the invention where such a combination is for the treatment of COPD, asthma or allergic rhinitis, a compound of formula Ia or Ib, or a pharmaceutically acceptable salt thereof, can be administered by inhalation or by the oral route and the other agent, e.g. xanthine (such as aminophylline or theophylline) can be administered by inhalation or by the oral route. A compound of formula Ia or Ib, or a pharmaceutically acceptable salt thereof, and the other agent, e.g xanthine may be administered together. They may be administered sequentially. Or they may be administered separately.

The following Examples illustrate the invention. The following abbreviations are used in the Examples:

The following Examples illustrate the invention. The following abbreviations are used in the Examples:

The following Examples illustrate the invention. The following abbreviations are used in the Examples:

| | |
|---|---|
| TFA | Trifluoroacetic acid; |
| THF | Tetrahydrofuran |
| DCM | Dichloromethane |
| HPLC | High Performance Liquid Chromatography; |
| LC/MS | Liquid Column Chromatography/Mass Spectroscopy; |
| GC | Gas Chromatography |
| SFC | Supercritical Fluid Chromatography |
| DMSO | Dimethylsulfoxide; |
| APCI-MS | Atmospheric Pressure Chemical Ionisation Mass Spectroscopy; |
| NMP | 1-methyl-2-pyrrolidinone |
| DIEA | N,N-diisopropylethylamine |
| HATU | O-(7-azabenzotriazol-1-yl)-N,N,N',N'-tetramethyluronium hexafluorophosphate |
| HBTU | 2-(1H-benzo[d][1,2,3]triazol-1-yl)-1,1,3,3-tetramethylisouronium hexafluorophosphate(V) |
| r.t. | Room temperature, which is a temperature in the range from of 16° C. to 25° C. |

SYNTHETIC EXPERIMENTAL

General Methods

NMR spectra were recorded on a Varian Mercury-VX 300 MHz instrument or a Varian Inova 400 MHz instrument. The central peaks of chloroform-d (H 7.27 ppm), acetone (H 2.05 ppm), dichloromethane-d2 (H 5.32 ppm) or DMSO-$d_6$ (H 2.50 ppm) were used as internal references. Alternatively, NMR spectra were recorded on a Varian Inova Unity 500 MHz instrument. Proton-NMR experiments were acquired using dual suppression of residual solvent peak and $H_2O$.

The following methods was used for chiral SFC analysis:

Using an Analytical Method Development System from Thar Technologies, Inc. Using $CO_2$ as mobile phase with MeOH as modifier and pressure at 150 bar. Columns used was kept at +37° C. by using an column oven. Detection was carried out on 254 nm.

Chiral SFC (method A): Chiralpak® AS, 0.46×25 cm column, 30% MeOH, 3 mL/min.

Chiral SFC (method B): Chiralpak® IB, 0.46×25 cm column, 35% MeOH, 2 mL/min.

The following method was used for LC/MS analysis:

Instrument Agilent 1100; Column Waters Symmetry 2.1×30 mm; Mass APCI; Flow rate 0.7 mL/min; Wavelength 254 nm; Solvent A: water+0.1% TFA; Solvent B: acetonitrile+0.1% TFA; Gradient 15-95%/B 2.7 min, 95% B 0.3 min.

The following method was used for GC-MS analysis:

Low resolution mass spectra and accurate mass determination were recorded on a Hewlett-Packard GC. MS system equipped with EI ionisation chamber, 70 eV.

The following method was used for HPLC analysis:

LC Method A: HPLC method A was performed with Agilent 1100 series machines on Kromassil© C18 5 µm 3.0×100 mm column. Aqueous phase was water/TEA (99.8/0.1) and organic phase was acetonitrile/TFA (99.92/0.08). Flow was 0.6 ml/min and gradient was set from 10 to 100% of organic phase during 20 minutes. Detection was carried out on 220, 254 and 280 nm.

LC Method B: HPLC method B was performed with Agilent 1100 series machines on XTerra® $RP_8$ 5 µm 3.0×100 mm column. Aqueous phase was 15 nM $NH_3$ in water and organic phase was acetonitrile. Flow was 0.6 ml/min and gradient was set from 10 to 100% of organic phase during 20 minutes. Detection was carried out on 220, 254 and 280 nm.

Preparative HPLC system A: Column: XBridge C18, dimension (150×30 mm, 5 µm packing), 20 ml/min solvent speed and gradient 20% to 90% MeCN (0.1 TFA) in Water (0.1% TFA) over 20 min)

Differential Scanning calorimetry: Using standard methods, for example those described in Höhne, G. W. H. et al (1996), Differential Scanning calorimetry, Springer, Berlin, the calorimetric response of a test sample to increasing temperature was investigated using a TA Instruments Q2000 Modulated Temperature Differential Scanning calorimeter (MTDSC) using a modulation of ±0.50° C. in intervals of 40 seconds and a ramp rate of 5° C. per minute. Approximately 1 mg of test sample was placed in aluminium cups with lids (no crimping) under a nitrogen atmosphere.

It is well known that the DSC onset and peak temperatures may vary due to the purity of the sample and instrumental parameters, especially the temperature scan rate. A person skilled in the art can use routine optimization/calibration to set up instrumental parameters for a differential scanning calorimeter so that data comparable to the data presented here can be collected.

Unless stated otherwise, starting materials were commercially available. All solvents and commercial reagents were of laboratory grade and were used as received.

Intermediate I1

Isobutyl 3-(5-iodo-1H-indazol-1-yl)benzoate (I1)

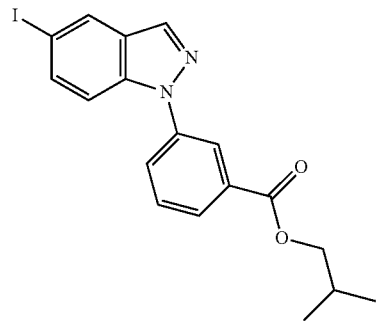 [SMILES: CC(C)COC(=O)c1cccc(-n2ncc3cc(I)ccc32)c1]

A 50 mL.s flask was charged with sodium carbonate (0.700 g, 6.60 mmol), 3-(5-iodo-1H-indazol-1-yl)benzoic acid (I1a) (2.185 g, 6 mmol) and NMP (15 mL) at 40° C. with magnetic stirring. After a couple of minutes 1-bromo-2-methylpropane (0.971 mL, 9.00 mmol) was added in one portion. After one hour at 40° C., the temperature was raised to 55° C. and another portion of 1-bromo-2-methylpropane (0.971 mL, 9.00 mmol) was added. The stirring was continued overnight. After cooling, the reaction mixture was partitioned between water and ethyl acetate. The organic phase was washed twice with water, dried over $Na_2SO_4$, filtered and evaporated to dryness to afford the title compound as a syrup (2.5 g, 99%). The product solidified to a beige material upon standing.

APCI-MS: m/z=421 [MH+]

$^1$H NMR (400 MHz, $CDCl_3$) δ 8.38 (1H, t), 8.19 (1H, d), 8.16 (1H, d), 8.07 (1H, dt), 7.92 (1H, ddd), 7.70 (1H, dd), 7.64 (1H, t), 7.56 (1H, d), 4.17 (2H, d), 2.12 (1H, m), 1.05 (6H, d).

LC (method A) rt=17.6 min 3-(5-Iodo-1H-indazol-1-yl)benzoic acid (I1a)

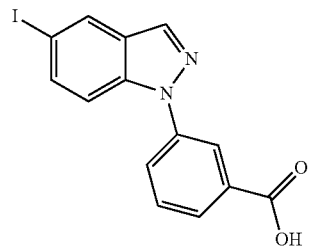 [SMILES: O=C(O)c1cccc(-n2ncc3cc(I)ccc32)c1]

3-(2-(2-Fluoro-5-iodobenzylidene)hydrazinyl)benzoic acid (I1b, 3.47 g, 9 mmol) and potassium tert, butoxide (2.3 g, 20.5 mmol) was stirred under argon atmosphere in NMP (45 mL) at 150° C. for 30 minutes. After cooling, the mixture was diluted with water (100 mL), acidified with aqueous HCl (1.7 M) and extracted trice with EtOAc. The combined organic phases were washed twice with water and then with brine. Evaporation of the organic phase afforded crude title compound (3.52 g, quant.) as a light brown, amorphous, gummy solid.

APCI-MS: m/z 365 [MH+]

¹H-NMR (300 MHz, DMSO-d₆): δ 13.2 (1H, b), 8.38 (1H, s), 8.33 (1H, s), 8.24 (1H, bs), 8.04 (1H, bd,), 7.97 (1H, d, further coupled), 7.81-7.68 (3H).

3-(2-(2-Fluoro-5-iodobenzylidene)hydrazinyl)benzoic acid (I1b)

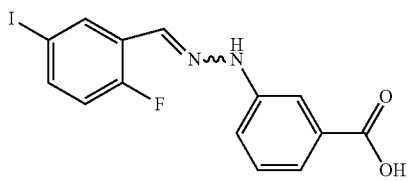 [SMILES: O=C(O)c1cccc(NN=Cc2cc(I)ccc2F)c1]

3-Hydrazinylbenzoic acid (1.52 g, 10 mmol)), 2-fluoro-5-iodobenzaldehyde (2.5 g, 10 mmol) and caesium carbonate (3.26 g, 10 mmol) were stirred in DMF (10 mL) at room temp under argon atmosphere for 2.5 h. Water (40 mL) was added and the clear solution was acidified with aqueous HCl (1.7 M). The beige-orange precipitate that formed was collected by, filtration, washed with water and dried in vacuo to give the title compound (3.75 g, 98%).

APCI-MS: m/z 385 [MH+]

¹H-NMR (300 MHz, DMSO-d₆): δ 119 (1H, b), 10.85 (1H, s), 8.17 (1H, dd), 7.94 (1H, s), 7.65 (1H, qd), 7.63-7.60 (2H), 7.40-7.31 (3H), 7.09 (1H, dd).

¹⁹F-NMR (300 MHz, DMSO-d₆, D₂O added): δ −123.4 (m).

Intermediate I2

(1R,2S)-2-amino-1-(2,3-dihydrobenzo[b][1,4]dioxin-6-yl)propan-1-ol hydrochloride. (I2)

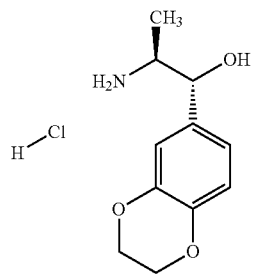

5-6 N HCl in 2-Propanol (8 mL, 40-48 mmol) was added to tert-butyl (1R,2S)-1-(2,3-dihydrobenzo[b][1,4]dioxin-6-yl)-1-hydroxypropan-2-ylcarbamate (I2a) (3.1 g, 10.02 mmol) in ethyl acetate (40 mL) at +40° C. and stirred at for 3 hours. The reaction mixture was allowed to reach room temperature and concentrated by evaporation. Ether was added and the salt was collected by filtration and washed with ether. The salt was found to be hygroscopic. Yield 2.10 g (85%)

APCI-MS: m/z 210 [MH+-HCl]

¹H-NMR (300 MHz, DMSO-d₆): δ 8.01 (brs, 3H), 6.87-6.76 (m, 3H), 5.93 (brd, 1H), 4.79 (brt, 1H), 4.22 (s, 4H), 3.32 (brm, 1H), 0.94 (d, 3H).

tert-butyl (1R,2S)-1-(2,3-dihydrobenzo[b][1,4]dioxin-6-yl)-1-hydroxypropan-2-ylcarbamate. (I2a)

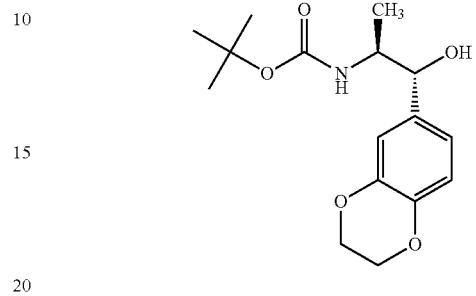

The diastereoselective catalytic Meerwein-Ponndorf-Verley reduction was made by the method described by Jingjun Yin et. al. *J. Org. Chem.* 2006, 71, 840-843. (S)-tert-butyl 1-(2,3-dihydrobenzo[b][1,4]dioxin-6-yl)-1-oxopropan-2-ylcarbamate (I2b) (3.76 g, 12.23 mmol), aluminium isopropoxide (0.5 g, 2.45 mmol) and 2-propanol (12 mL, 157.75 mmol) in toluene (22 mL) was stirred at +50° C. under argon for 16 hours. The reaction mixture was poured into 1M HCl (150 mL), the mixture was extracted with EtOAc (250 mL). The organic phase was washed with water (2×50 mL) and brine (100 mL), dried over Na₂SO₄, filtered and concentrated. The crude product was purified by flash-chromatography on silica using EtOAc:Hexane (1:2) as eluent. Fractions containing product was combined. Solvent was removed by evaporation to give the desired product as a colourless solid. Yield 3.19 g (84%)

APCI-MS: m/z 236, 210, 192 [MH+-tBu-18, MH+-BOC, MH+-BOC-18]

¹H NMR. (300 MHz, DMSO-d₀): δ 6.80-6.70 (m, 3H), 6.51 (d, 1H), 5.17 (d, 1H), 4.36 (t, 1H), 4.19 (s, 4H), 3.49 (m, 1H), 1.31 (s, 9H), 0.93 (d, 3H).

(S)-tert-butyl 1-(2,3-dihydrobenzo[b][1,4]dioxin-6-yl)-1-oxopropan-2-ylcarbamate. (I2b)

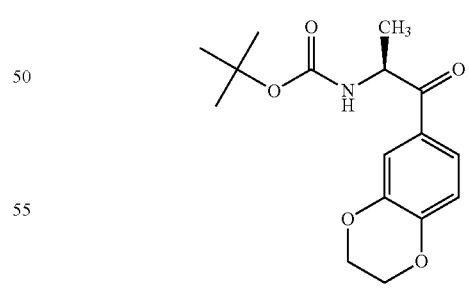

A suspension of (S)-tert-butyl 1-(methoxy(methyl)amino)-1-oxopropan-2-ylcarbamate (3 g, 12.92 mmol) in THF (30 mL) was placed under a protective atmosphere of Argon and cooled down to −15 to −20° C., isopropylmagnesium chloride, 2M in THF (6.5 mL, 13.00 mmol) was added keeping the temperature below −10° C. The slurry started to dissolve, temperature was allowed to reach 0° C., a freshly prepared solution of (2,3-dihydrobenzo[b][1,4]dioxin-6-yl)

magnesium bromide, 0.7M in THF (20 mL, 14.00 mmol) was added. The temperature was allowed to reach room temperature, the reaction mixture was stirred for 17 hours. 1N HCl (300 mL) was cooled on icebath to +10° C., the reaction mixture was poured into the acidic water solution, TBME=tert-butyl methyl ether (300 mL) was added and the mixture was transferred to a separation funnel. The water-phase was backextracted with TBME (200 mL). The ether phases were washed with water, brine and dried ($Na_2SO_4$).

The crude product was purified by flash chromatography using TBME:Heptane=1:2 as eluent. Fractions containing the product was combined and solvents was removed by evaporation to give the subtitle compound as a slightly yellow sticky oil/gum. Yield 3.76 g (95%)

APCI-MS: m/z 208 [$MH^+$-BOC]

$^1$H NMR (300 MHz, DMSO-$d_6$): δ 7.50 (dd, 1H), 7.46 (d, 1H), 7.24 (d, 1H), 6.97 (d, 1H), 4.97 (m, 1H), 4.30 (m, 4H), 1.36 (s, 9H), 1.19 (d, 3H).

Intermediate I3

(1R,2S)-2-amino-1-(4H-benzo[d][1,3]dioxin-7-yl)propan-1-ol hydrochloride (I3)

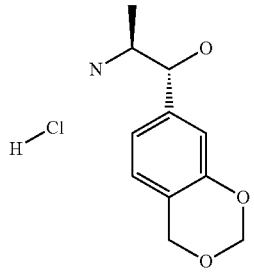

Tert-butyl (1R,2S)-1-(4H-benzo[d][1,3]dioxin-7-yl)-1-hydroxypropan-2-ylcarbamate (I3b) (403 mg, 1.30 mmol) was dissolved in ethyl acetate (5 mL), 5-6 N HCl solution in 2-propanol (1.5 mL, 7.5-9 mmol) was added. The mixture was stirred at +50° C. for 1.5 hours. The solvents was removed by evaporation, the residual sticky gum was treated with EtOAc and evaporated again to give a solid material that was suspended in MeCN and stirred for a few minutes. The solid colourless salt was collected by filtration and was found to be somewhat hygroscopic, the salt was quickly transferred to an dessicator and dried under reduced pressure. Yield 293 mg (92%)

APCI-MS: m/z 210 [$MH^+$-HCl]

$^1$H NMR (300 MHz, DMSO-$d_6$) δ 8.07 (3H, s), 7.05 (1H, d), 6.92 (1H, dd), 6.85 (1H, d), 6.03 (1H, d), 5.25 (2H, s), 4.87 (3H, m), 3.42-3.29 (1H, m), 0.94 (3H, d).

(4S,5R)-5-(4H-benzo[d][1,3]dioxin-7-yl)-4-methyloxazolidin-2-one (I3a)

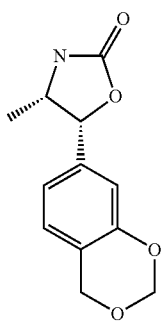 [SMILES: C[C@@H]1NC(=O)O[C@@H]1c1ccc2c(c1)OCOC2]

A mixture of (1R,2S)-2-amino-1-(4H-benzo[d][1,3]dioxin-7-yl)propan-1-ol hydrochloride (I3b) (120 mg, 0.49 mmol), DIEA (0.100 mL, 0.59 mmol) and CDI (90 mg, 0.56 mmol) in THF (2 mL) was stirred at room temperature for 2 hours. The reaction mixture was concentrated by evaporation, the residual material was partitioned between EtOAc and water, the organic phase was washed with 10% $NaHSO_4$, dried over $MgSO_4$, filtered and evaporated. The crude product was analysed by LC/MS and was considered pure enough for further analysis by NMR. Yield 66 mg (57%)

The relative cis conformation of the product was confirmed by comparing the observed $^1$H-NMR with the literature values reported for similar cyclisised norephedrine (Org. Lett. 2005 (07), 13, 2755-2758 and Terahedron Assym. 1993, (4), 12, 2513-2516). In a 2D NOESY experiment was observed a strong NOE cross-peak for the doublett at 5.64 with the multiplet at 4.19 ppm, this also confirmed the relative cis-conformation.

APCI-MS: m/z 236 [$MH^+$]

$^1$H NMR (400 MHz, $CDCl_3$) δ 6.99 (d, J=8.0 Hz, 1H), 6.88 (dd, J=8.0, 1.4 Hz, 1H), 6.83 (s, 1H), 5.81 (brs, 1H), 5.64 (d, J=8.0 Hz, 1H), 5.26 (s, 2H), 4.91 (s, 2H), 4.19 (m, 1H), 0.85 (d, J=6.4 Hz, 3H).

Tert-butyl (1R,2S)-1-(4H-benzo[d][1,3]dioxin-7-yl)-1-hydroxypropan-2-ylcarbamate (I3b)

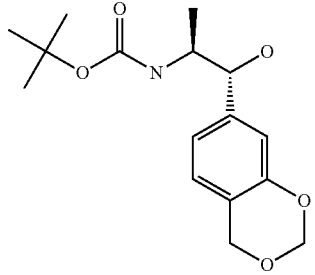 [SMILES: C[C@H](NC(=O)OC(C)(C)C)[C@H](O)c1ccc2c(c1)OCOC2]

A mixture (S)-tert-butyl 1-(4H-benzo[d][1,3]dioxin-7-yl)-1-oxopropan-2-ylcarbamate (I3c) (680 mg, 2.21 mmol), tri-isopropoxyaluminum (140 mg, 0.69 mmol) and propan-2-ol (3 mL, 38.9 mmol) in toluene (3 mL) was stirred at +65° C. for 15 hours. The reaction mixture was allowed to cool down and poured into 1M HCl (50 mL) and extracted with EtOAc (2×50 mL). The organic phase was washed with water, brine, dried over $MgSO_4$, filtered and solvents removed by evaporation to afford a crude product as a colourless solid. The crude product was first purified by Flash chromatography, (solvent A=Heptane, solvent B=EtOAc+10% MeOH). An gradient of 10% B to 50% B in A was used. The obtained product was crystallised from DCM/Heptane to afford the subtitle compound colourless needles. Yield 414 mg (60%)

APCI-MS: m/z 210 [$MH^+$-BOC]

$^1$H NMR (400 MHz, DMSO-$d_6$) δ 6.97 (1H, d), 6.88 (1H, d), 6.77 (1H, s), 6.56 (1H, d), 5.27 (1H, d), 5.22 (2H, s), 4.83 (2H, s), 4.44 (1H, t), 3.53 (1H, m), 1.32 (9H, s), 0.93 (3H, d).

(S)-Tert-butyl 1-(4H-benzo[d][1,3]dioxin-7-yl)-1-oxopropan-2-ylcarbamate (I3c)

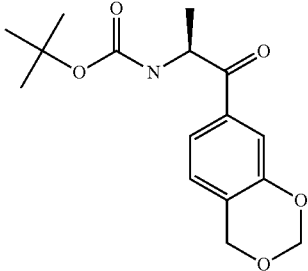 [SMILES: C[C@H](NC(=O)OC(C)(C)C)C(=O)c1ccc2c(c1)OCOC2]

7-Bromo-4H-benzo[d][1,3]dioxine (1 g, 4.65 mmol) was dissolved in THF (5 mL) and added to magnesium (0.113 g, 4.65 mmol) under a protective atmosphere of argon, one small iodine crystal was added, the coloured solution was heated with an heatgun in short periods to initiate the grignard formation, when the iodine coluor vanished the reaction was allowed to proceed at room temperature for 1.5 hours.

In a separate reaction tube was (S)-tert-butyl 1-(methoxy (methyl)amino)-1-oxopropan-2-ylcarbamate (1 g, 4.31 mmol) suspended in THF (5 mL) and cooled in an ice/acetone bath to below −5° C., isopropylmagnesium chloride, 2M solution in THF (2.5 mL, 5.00 mmol) was slowly added to form an solution. To this solution was added the above freshly prepared grignard reagent. The mixture was allowed to reach room temperature and stirred for 4 hours. The reaction mixture was slowly poured into ice-cold 150 mL 1M HCl, EtOAc (150 mL) was added and the mixture was stirred for a few minutes and transferred to a separation funnel. The organic phase was washed with water and brine, dried over MgSO4, filtered and concentrated. The obtained crude product was further purified by flash chromatography using an prepacked 70 g silica column with gradient of 10% TBME to 40% TBME in Heptane as eluent. The subtitle compound was obtained as a colourless solid. Yield 790 mg (59%)

APCI-MS: m/z 208 [MH$^+$-BOC]

$^1$H NMR (400 MHz, DMSO-d$_6$) δ 7.53 (1H, dd), 7.39 (1H, s), 7.30 (1H, d), 7.22 (1H, d), 5.30 (2H, s), 4.98 (1H, m), 4.95 (2H, s), 1.35 (9H, s), 1.20 (3H, d).

Intermediate I4

3-(5-((1R,2S)-2-(2,2-difluoropropanamido)-1-(2,3-dihydrobenzo[b][1,4]dioxin-6-yl)propoxy)-1H-indazol-1-yl)benzoic acid (I4)

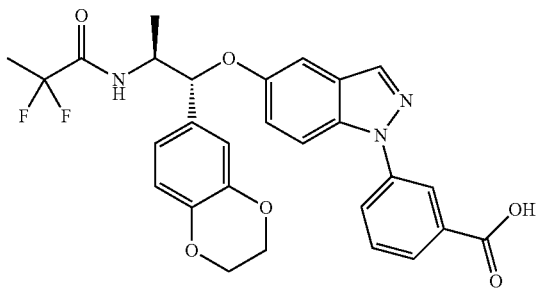 [SMILES: C[C@H](NC(=O)C(C)(F)F)[C@H](Oc1ccc2c(cnn2-c2cccc(C(=O)O)c2)c1)c1ccc2c(c1)OCCO2]

A solution of isobutyl 3-(5-((1R,2S)-2-(2,2-difluoropropanamido)-1-(2,3-dihydrobenzo[b][1,4]dioxin-6-yl)propoxy)-1H-indazol-1-yl)benzoate (I4a) (350 mg, 0.59 mmol) in THF (5 mL) and acetonitrile (2 mL) was treated with 0.25 M NaOH (4.72 mL, 1.18 mmol). The mixture was stirred at ambient temperature for 23 hours, additional 1M NaOH (0.590 mL, 0.59 mmol) was added and the mixture was stirred at +45° C. for 2 hours. The reaction mixture was allowed to cool down and acidified to pH 2.5-3 by adding 1 N HCl. Addition of THF and MeCN until solution followed by purification by HPLC, using an Kromasil 100-10-C18, 50×250 mm column, an 30 min gradient from 50% to 90% MeCN in water+0.1% TFA in solvents with flow=40 mL/min and UV=254 nm to collect fractions. Fractions containing the product was combined and freeze dried. The material was redissolved in tBuOMe, addition of Heptane gave precipitation, the formed slurry was evaporated to afford the subtitle compound as a colourless solid. Yield 315 mg (99%)

APCI-MS: m/z 538 [MH$^+$]

$^1$H NMR (300 MHz, DMSO-d$_6$) δ 13.27 (1H, s), 8.66 (1H, d), 8.25 (1H, d), 822 (1H, t), 8.00 (1H, ddd), 7.92 (1H, dt), 7.77 (1H, d), 7.69 (1H, t), 7.22 (1H, dd), 7.14 (1H, d), 6.89-6.78 (3H, m), 5.17 (1H, d), 4.22-4.11 (5H, m), 1.54 (3H, t), 1.29 (3H, d).

Isobutyl 3-(5-((1R,2S)-2-(2,2-difluoropropanamido)-1-(2,3-dihydrobenzo[b][1,4]dioxin-6-yl)propoxy)-1H-indazol-1-yl)benzoate (I4a)

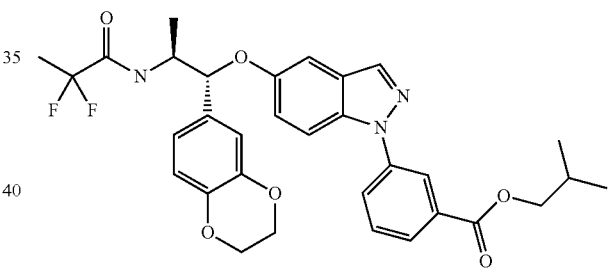

Isobutyl 3-(5-((1R,2S)-2-amino-1-(2,3-dihydrobenzo[b][1,4]dioxin-6-yl)propoxy)-1H-indazol-1-yl)benzoate (Mb) (0.5 g, 1.00 mmol), 2,2-difluoropropanoic acid (0.16 g, 1.45 mmol) and HBTU (0.567 g, 1.50 mmol) in DCM (4 mL) was treated with DIEA (0.696 mL, 3.99 mmol), the mixture was stirred at ambient temperature for 1 hour. The reaction was quenched by addition 10% NaHSO4(aq), brine was added to help phase separation. The lower red DCM phase was separated, the waterphase was extracted with one portion of EtOAc, the combined organic solutions were dried over MgSO4 and filtered, solvents was removed by evaporation. Obtained a crude product as red oil. The crude material was further purified by flash chromatography using an 70 g prepacked silica column, an gradient of 0% to 50% EtOAc in Heptane was applied. Fractions with product was combined and solvents was removed by evaporation. An slightly yellow sticky oil was obtained after final evaporation from DCM. Yield 540 mg (91%).

APCI-MS: m/z 594 [MH$^+$]

$^1$H NMR (300 MHz, DMSO-d$_6$) δ 8.65 (1H, d), 8.26 (1H, d), 8.25 (1H, t), 8.05 (1H, ddd), 7.95 (1H, dt), 7.78 (1H, d), 7.73 (1H, t), 7.22 (1H, dd), 7.14 (1H, d), 6.90-6.77 (3H, m), 5.17 (1H, d), 4.18 (4H, s), 4.15 (1H, m), 4.12 (2H, d), 2.05 (1H, m), 1.55 (3H, t), 1.29 (3H, d), 0.99 (6H, d).

Isobutyl 3-(5-((1R,2S)-2-amino-1-(2,3-dihydrobenzo[b][1,4]dioxin-6-yl)propoxy)-1H-indazol-1-yl)benzoate (I4b)

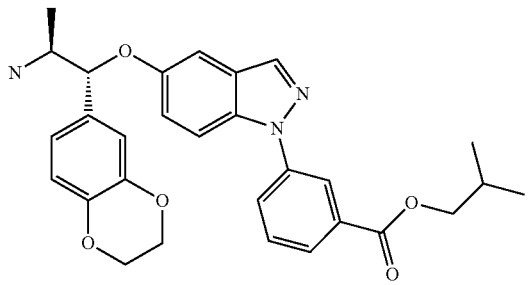 [SMILES: CC(C)COC(=O)c1cccc(-n2ncc3cc(O[C@H](c4ccc5c(c4)OCCO5)[C@H](C)N)ccc32)c1]

A mixture of cesium carbonate (78 g, 240.00 mmol), (1R,2S)-2-amino-1-(2,3-dihydrobenzo[b][1,4]dioxin-6-yl)propan-1-ol hydrochloride (I4c) (19.66 g, 80.00 mmol), 2-(dimethylamino)acetic acid (4.12 g, 40.00 mmol) and copper(I) iodide (0.678 ml, 20.00 mmol) in butyronitrile (188 ml) was stirred at 115° C. for 60 min under a protective atmosphere of argon in 1 L round bottom-flask. A solution of isobutyl 3-(5-iodo-1H-indazol-1-yl)benzoate (I1) (33.6 g, 80 mmol) in butyronitrile (62.6 ml) was generated by heating at 80° C. for 20 minutes in 250 mL round bottom-flask. The solution was pumped to the above mixture within 2-3 minutes. The vessel was rinsed with further butyronitrile (15.6 ml) which also was added. The grayish reaction mixture was sealed and stirred at 115° C. for 45 hours. The cooled reaction mixture was extracted between water (500 mL) and ethyl acetate (1.5 L). The organic phase was washed with water (3×700 mL) and the solvents removed by reduced pressure affording 38 g of a gummy greenish residue. The crude product dissolved in approx 60-70 mL DCM before loading the column, Flash chromatography on silica (d=13 cm, l=18 cm) first using ethyl acetate:heptane 1:1 with 2% TEA (6 L), (so the starting materials+the N-alkylated product eluted), ethyl acetate:heptane 3:1 with 2% TEA (8 L) and then washed the column with—ethyl acetate (12 L) with 2% TEA, 600 mL fractions collected product mostly in fr 28-44, evaporated to dryness at 45° C. for 1 h affording 16.42 g of the product.

HNMR showed a pure product, contained some ethyl acetate (<5% by weight). HPLC purity >95%. Yield 16.42 g (41%)

APCI-MS: m/z 502 [MH$^+$]

$^1$H NMR (400 MHz, DMSO-d$_6$) δ 8.24 (2H, m), 8.05 (1H, ddd), 7.94 (1H, dt), 7.77-7.72 (2H, m), 7.22 (1H, dd), 7.17 (1H, d), 6.88 (2H, m), 6.81 (1H, d), 4.97 (1H, d), 4.19 (4H, s), 4.12 (2H, d), 3.11 (1H, m), 2.05 (1H, m), 1.35 (2H, bs), 1.07 (3H, d), 0.99 (6H, d).

LC (method A) rt=12.3 min
LC (method B) rt=14.2 min

Intermediate 5

3-(5-((1R,2S)-1-(4H-Benzo[d][1,3]dioxin-7-yl)-2-(2,2-difluoropropanamido)propoxy)-1H-indazol-1-yl)benzoic acid (I5)

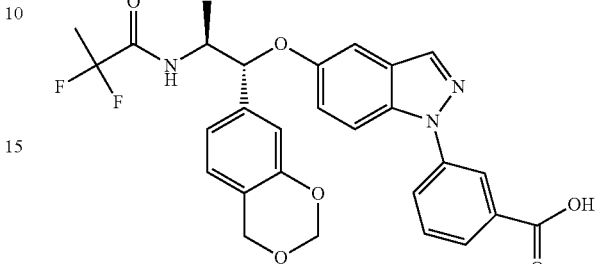

Isobutyl 3-(5-((1R,2S)-1-(4H-benzo[d][1,3]dioxin-7-yl)-2-(2,2-difluoropropanamido)propoxy)-1H-indazol-1-yl)benzoate (I5a) (398 mg, 0.67 mmol) was dissolved in methanol (3 mL) and THF (3.0 mL). Lithium hydroxide (0.032 mL, 2.01 mmol) dissolved in water (2.5 mL) was added. A clear slightly pink solution was obtained. After 2 h the solution was ice-cold. Ethyl acetate was added and then hydrochloric acid (1M) to acidic pH. The water phase was once more extracted with ethyl acetate. The collected organic phases were dried over magnesium sulfate and evaporated. It was dissolved in methanol and the solution was applied onto a 1 g SCX column. The methanol eluate (ca 15 mL) was concentrated. Freeze-drying from acetonitrile/water gave the title compound (362 mg, 100%).

APCI-MS: m/z 538 [MH$^+$]

$^1$H NMR (400 MHz, CD$_2$Cl$_2$) δ 8.40 (1H, t), 8.05 (1H, dt), 8.02 (1H, d), 7.98 (1H, ddd), 7.70 (1H, d), 7.65 (1H, t), 7.22 (1H, dd), 7.02 (1H, d), 7.00 (1H, d), 6.91 (1H, s), 6.67 (1H, s), 5.22 (2H, q), 4.87 (2H, s), 4.46-4.36 (1H, m), 1.75 (3H, t), 125 (3H, d).

Isobutyl 3-(5-((1R,2S)-1-(4H-benzo[d][1,3]dioxin-7-yl)-2-(2,2-difluoropropanamido)propoxy)-1H-indazol-1-yl)benzoate (I5a)

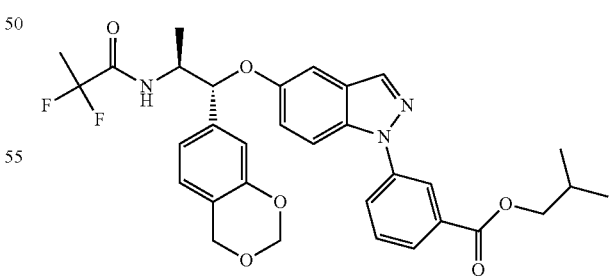

A mixture of isobutyl 3-(5-((1R,2S)-2-amino-1-(4H-benzo[d][1,3]dioxin-7-yl)propoxy)-1H-indazol-1-yl)benzoate (420 mg, 0.84 mmol) (I5b), 2,2-difluoropropanoic acid (213 mg, 1.94 mmol) and HBTU (420 mg, 1.11 mmol) were suspended in dichloromethane (10 mL). N-ethyl-N-isopropylpropan-2-amine (0.85 mL, 5.13 mmol) was added and the mixture was stirred at room temperature overnight. Water (ca 10 mL) was added to the solution. After stirring for some minutes the mixture was added to a phase separator. The water phase was stirred with dichloromethane (5 mL) and added to the phase separator. The combined organic phases were concentrated to a brown oil. Purification by flash chromatography on silica (dichloromethane/ethyl acetate 10/1) gave the title compound as a white foam (400 mg, 80%).

APCI-MS: m/z 594 [MH+]

$^1$H NMR (400 MHz, DMSO-$d_6$) δ 8.71 (1H, d), 8.27-8.23 (2H, m), 8.07-8.03 (1H, m), 7.95 (1H, d), 7.78 (1H, d), 7.73 (1H, t), 7.23 (1H, dd), 7.14 (1H, d), 7.04-6.96 (2H, m), 6.86 (1H, s), 5.26-5.17 (3H, m), 4.82 (2H, s), 4.24-4.15 (1H, m), 4.12 (2H, d), 2.11-2.00 (1H, m), 1.56 (3H, t), 1.30 (3H, d), 0.99 (6H, d)

Isobutyl 3-(5-((1R,2S)-2-amino-1-(4H-benzo[d][1,3]dioxin-7-yl)propoxy)-1H-indazol-1-yl)benzoate (I5b)

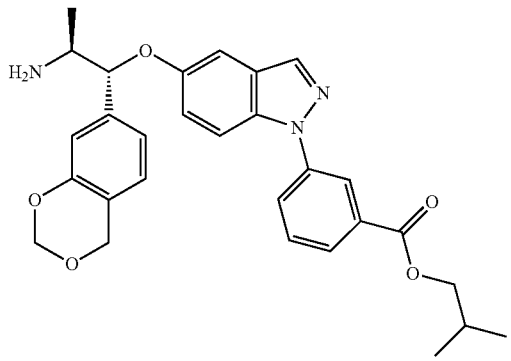 [SMILES: CC(C)COC(=O)c1cccc(-n2ncc3cc(O[C@H](c4ccc5c(c4)OCOC5)[C@H](C)N)ccc32)c1]

A 250 mL one-neck round bottomed-flask with magnetic stirring and argon atmosphere was charged with cesium carbonate (30.3 g, 93.00 mmol), (1R,2S)-2-amino-1-(4H-benzo[d][1,3]dioxin-7-yl)propan-1-ol hydrochloride (I3) (7.37 g, 30.00 mmol), 2-(dimethylamino)acetic acid (1.547 g, 15.00 mmol), copper(I) iodide (1.428 g, 7.50 mmol) and butyronitrile (72 mL) and heated at 110° C. for 30 min. A solution of isobutyl 3-(5-iodo-1H-indazol-1-yl)benzoate (I1) (12.61 g, 30 mmol) in butyronitrile (12.00 mL) was generated by heating at 80° C. for 10 minutes. The solution was pumped to the above mixture within 3 minutes. The vessel was rinsed with further butyronitrile (6.00 mL) which also was added. The reaction mixture was sealed and stirred at 110° C. for 19 h. The reaction mixture was cooled and extracted between water and ethyl acetate (1 L). The organic phase was washed three times with water (3×500 mL), dried over magnesium sulfate and concentrated. The residue was purified by flash chromatography on silica using ethyl acetate:heptane 1:1 with 2% TEA followed by ethyl acetate:heptane 3:1 with 2% TEA and finally with ethyl acetate with 2% TEA. This gave the title compound (5.1 g, 34%).

APCI-MS: m/z 502.2 [MH+]

$^1$H NMR (400 MHz, DMSO-$d_6$) δ 8.25 (1H, t), 8.23 (1H, s), 8.05 (1H, ddd), 7.94 (1H, dt), 7.78-7.70 (2H, m), 7.24 (1H, dd), 7.17 (1H, d), 7.01 (2H, m), 6.89 (1H, s), 5.22 (2H, dd), 5.05 (1H, d), 4.83 (2H, ds), 4.11 (2H, d), 3.15 (1H, m), 2.05 (1H, m), 1.39 (2H, bs), 1.07 (3H, d), 0.98 (6H, d).

LC (method A) rt=10.6 min
LC (method B) rt=12.2 min

Intermediate I6

(S)-(−)-tetrahydrothiophene-3-amine-1,1-dioxide hydrochloride (I6)

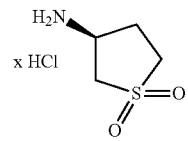

(S)-(−)-N-(1,1-dioxidotetrahydrothiophen-3-yl)benzamide (I6a) (7.08 g) was suspended in aqueous 5M HCl (250 mL). The mixture was heated at 130° C. for 13 hours. After cooling in an ice-bath solid benzoic acid was removed by filtration and washed with 1M aqueous HCl, the combined filtrates were evaporated to dryness. The residue was re-suspended in 1,4-dioxane (40 mL), the colourless solid subtitle compound was isolated by filtration, washed with dioxane (10 mL) and dried to constant weight. Yield 4.99 g (98%).

$^1$H NMR (400 MHz, D$_2$O): δ 4.12 (1H, pent, further coupled), 3.60 (1H, dd), 3.38 (1H, m), 3.27-2.15 (2H), 2.64 (1H, m), 2.21 (1H, m).

[α]$_D$ −13.5° (c=1.1, H$_2$O)

(S)-(−)-N-(1,1-dioxidotetrahydrothiophen-3-yl)benzamide (I6a)

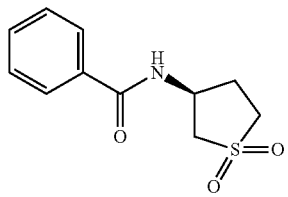 [SMILES: O=C(N[C@H]1CCS(=O)(=O)C1)c1ccccc1]

(S)—N-(tetrahydrothiophen-3-yl)benzamide (I6b) (7.1 g) was dissolved in EtOAc (1.2 L). Sat. aqueous NaHCO$_3$ (0.6 L) was added. 3-chlorobenzoperoxoic acid (77%, 27 g) was added in portions during 10 min. Stirring was continued for 4 hours then dimethylsulphide (3.5 mL) was added and the stirring was continued for additional 100 min. to completely destroy excess m-chloroperbenzoic acid. The phases were separated, the organic phase was washed twice with water and evaporated at reduced pressure. The colourless residue was re-crystallized from EtOAc (~350 mL) to yield pure subtitle compound (6.3 g). The mother liq. was evaporated and re-crystallized from EtOAc to give additional product (0.72 g). Total yield 7.02 g (85.7%)

$^1$H NMR (400 MHz, DMSO-$d_6$): δ 8.74 (1H, d), 7.88-7.84 (2H), 7.55 (1H, t, further coupled), 7.51-7.45 (2H), 4.70 (1H, sext), 3.50 (1H, dd), 3.37 (1H, ddd), 125-3.15 (1H m), 3.97 (1H, dd), 2.44 (1H, sext.), 228-2.16 (1H, m).

[α]$_D$=−39.8° (c=1.0, MeOH)

(S)-(−)-N-(tetrahydrothiophen-3-yl)benzamide (I6b)

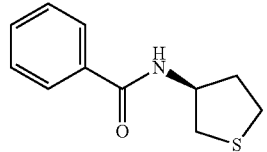 [SMILES: O=C(N[C@H]1CCSC1)c1ccccc1]

A 1.36M stock solution of HCl in AcOH was prepared from 100 ml AcOH, 11 mL AcCl and 2.8 mL H$_2$O (slightly exothermic hydrolysis).

(S)-(−)-4-[2-(methylsulfanyl)ethyl]-2-phenyl-4,5-dihydro-1,3-oxazole (I6c) (1.7 g) was dissolved in 25 mL of acetic acid being 1.36 M in respect to HCl. The solution was heated at 130° C. for 18 hs. GC-MS: shows complete reaction. Highest MS ion is 146 (M-61 fragment). The reaction mixture was then cooled and freeze dried to afford the subtile compound as a colourless fluffy solid. Yield 1.59 g (100%)

$^1$H NMR (400 MHz, DMSO-d$_6$): δ 8.41 (1H, d, NH), 7.86-7.82 (2H), 7.53 (1H, m), 7.49-7.43 (2H), 4.49 (1H, sext.), 3.03 (1H, dd), 2.96-2.88 (1H, m), 2.88-2.80 (1H, m), 2.75 (1H, dd), 2.19-2.10 (1H, m), 2.07-1.97 (1H, m).

[α]$_D$ −32.4° (c=0.95, MeOH)

(S)-(−)-4-[2-(methylsulfanyl)ethyl]-2-phenyl-4,5-dihydro-1,3-oxazole (I6c)

The described procedure is a somewhat modified, optimized and complementary one to the literature synthesis of 3-aminotetrahydrotiophene enantiomer(s):
1. Dehmlow & Westerheide Synthesis 1992, 947-949
2. Ashton et al Bioorg Med Chem Lett 17 (2007) 6779-6784

L-(S)-2-amino-4-(methylthio)butan-1-ol (10.0 g) and zinc (II) bromide (0.5 g) were mixed in benzonitrile (18 mL). The mixture was stirred at 120° C. for 45 hours, the major part of the excess benzonitrile was distilled off by Kugelrohr distillation, The residue was diluted with a small volume of CH$_2$Cl$_2$ and subjected to autoflash chromatography on SiO$_2$ (330 g) using a gradient of 0-70% EtOAc in Heptane to afford the subtitle compound as an oil. Yield 12.09 g (74%).

$^1$H NMR (300 MHz, DMSO-d$_6$): δ 7.81-7.75 (2H), 7.50-7.42 (1H, m), 7.42-7.34 (2H), 4.42 (1H, dd), 4.29-4.18 (1H, m), 3.98 (1H, t), 2.60-2.45 (2H), 1.99 (3H, s), 1.80-1.66 (2H).

[α]$_D$=−89.8° (c=1.5, EtOAc)

Intermediate 7

(R)-(+)-tetrahydrothiophene-3-amine-1,1-dioxide hydrochloride (I7)

The subtitle compound was prepared similarly as described for compound (I6), but starting from (R)—N-(1,1-dioxidotetrahydrothiophen-3-yl)benzamide (I7a) (3.0 g). Yield 2.10 g (98%).

[α]$_D$=+12.5° (c=1.1, H$_2$O)

1H-NMR (400 MHz, DMSO-d6) δ 4.13 (1H, pent), 3.61 (1H, dd), 3.39 (1H, m), 3.27-3.17 (2H), 2.65 (1H, dtd), 2.29-2.16 (2H).

(R)—N-(1,1-dioxidotetrahydrothiophen-3-yl)benzamide (I7a)

The subtitle compound was prepared similarly as described for compound (I6a), but starting from (R)—N-(tetrahydrothiophen-3-yl)benzamide (I7b) (3.06 g). Yield 3.0 g (85.5%).

[α]$_D$ +40.1° (c=1.0, MeOH)
H NMR (400 MHz, DMSO-d$_6$) δ 8.74 (1H, d), 7.88-7.83 (2H), 7.55 (1H, t, further coupled), 7.48 (2H, t, further coupled), 4.69 (1H, sext.), 3.50 (1H, dd), 3.37 (1H, m), 3.20 (1H, ddd), 3.07 (1H, dd), 2.28-2.16 (1H, m).

(R)—N-(tetrahydrothiophen-3-yl)benzamide (I7b)

The subtitle compound was prepared similarly as described for compound (I6b), but starting from (R)-4-(2-(methylthio)ethyl)-2-phenyl-4,5-dihydrooxazole (I7c) (3.04 g).
Yield 2.78 g (98%).

[α]$_D$ +32.2° (c=1.1, MeOH)
$^1$H NMR (400 MHz, DMSO-d$_6$) δ 8.41 (1H, d), 7.87-7.81 (2H, m), 7.53 (1H, m), 7.49-7.42 (2H, m), 4.49 (1H, sextet), 3.03 (1H, dd), 2.96-2.88 (1H, m), 2.88-2.80 (1H, m), 2.75 (1H, dd), 2.19-2.09 (1H, m), 2.07-1.96 (1H, m).

(R)-4-(2-(methylthio)ethyl)-2-phenyl-4,5-dihydrooxazole (I7c)

The subtitle compound was prepared similarly as described for compound (I6c), but starting from D-(R)-2-amino-4-(methylthio)butan-1-ol (7.75 g). Yield 3.04 g (24%).

[α]$_D$=+ 89.8° (c=1.5, EtOAc)

$^1$H NMR (400 MHz, DMSO-d$_6$) δ 7.89-7.84 (2H, m), 7.57-7.51 (1H, m), 7.50-7.44 (2H, m), 4.51 (1H, dd), 4.32 (1H, dq), 4.07 (1H, t), 2.60 (2H, m), 2.07 (3H, s), 1.81 (2H, m).

Intermediate 8

(S)-(-)-3-Aminotetrahydrothiphenesulphoxide hydrochloride (epimeric mixture) (I8)

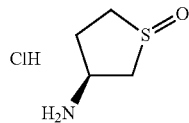

(S)—N-(1-dioxidotetrahydrothiophen-3-yl)benzamide (I8a) (1.7 g, 7.61 mmol) was dissolved in 5M aqueous HCl (140 mL) and stirred at (block temp.) 130° C. After 1 hour 15 minutes the temperature was lowered to +70° C. and the mixture was stirred at this temperature for additional 11 hours 45 minutes, thereafter allowed to reach room temperature. The mixture was cooled in an ice-bath, crystalline precipitated benzoic acid was removed by filtration, the filtrate was evaporated to leave sticky gum. The material was dissolved in water and washed with 3×CH$_2$Cl$_2$, the waterphase was evaporated, the residue was co-evaporated with EtOH-Toluene a couple of times and treated the semisolid residue with EtOH to form a suspension that was stirred at ambient temperature for 25 minutes. The beige solid salt was collected by filtration to afford 200 mg crude product (batch 1). Additional 82 mg (batch 2) material crystallised from the mother liquid. NMR analysis of the two batches revealed that racemization had taken place. No more purifications was made on these crude batches, they were both used as obtained.
batch 1:
$^1$H NMR (400 MHz, D$_2$O) δ 4.32 (0.88H, m), 4.14 (0.12H, m), 3.43-3.19 (2H, m), 3.14-2.95 (2H, m), 2.83-2.66 (1H, m), 2.58-2.47 (0.12H, m), 2.23 (0.89H, m), batch 2:
$^1$H NMR (400 MHz, D$_2$O) δ 4.32 (0.18H, m), 4.14 (0.82H, m), 3.43-3.18 (2H, m), 3.13-2.85 (2H, m), 2.81-2.65 (1H, m), 2.58-2.45 (0.81H, m), 2.22 (0.19H, m).

(S)—N-(1-dioxidotetrahydrothiophen-3-yl)benzamide (I8a)

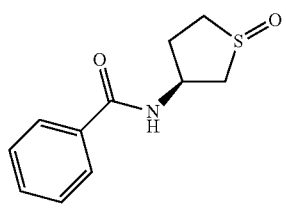 [SMILES: O=C(N[C@H]1CCS(=O)C1)c1ccccc1]

(S)-(-)-N-(tetrahydrothiophen-3-yl)benzamide (I6a) (2.81 g, 13.56 mmol) was dissolved in acetonitrile (150 mL). A heteropolyacid pyridinium salt catalyst (360 mg) (PMo$_{11}$VO$_{40}$H$_4$×1.77 pyridine, prepared according to Gustavo P. Romanelli et. al, Synlett 2005, 1, 75-78) was added followed by hydrogen peroxide (35%, 1.15 mL). The mixture was stirred at ambient temperature, after 2.5 hours additional catalyst (100 mg) was added and the reaction was allowed to proceed for another 2 hours. Me$_2$S (0.115 mL) was added, after 25 minutes the mixture was filtered and tested positive for peroxide. Additional Me$_2$S (0.6 mL) was added and the mixture was stirred over night at ambient temperature. Water (50 mL) and 2 g sodium bisulphite was added and the mixture was stirred for 30 min. Solvents was evaporated to about half volume, diluted with water and extracted with 3×EtOAc. The combined organic phases were washed with water and brine and evaporated to leave a white solid. The obtained solid was re-crystallized from EtOAc (~70 mL) to yield 1.39 g of isomerically pure sulphoxide (batch 1)

The mother liq. was evaporated and subjected to flash chromatography on SiO2 (20 g) 0-70% MeOH in EtOAc. Additional 365 mg (batch 2) isomerically pure sulphoxide was isolated. Also isolated were 145 mg material containing an 3:2 epimeric mixture of the sulphoxide. The major formed isomerically pure sulphoxide batches 1 and 2 were combined to afford a total of 1.75 g (58%)

$[α]_D$=-91.9° (c=1, MeOH)
$^1$H NMR (400 MHz, CD$_3$OD) δ 7.83 (2H, m), 7.54 (1H, m), 7.47 (2H, m), 4.90 (1H, m), 3.52 (1H, dd), 3.19-3.02 (2H, m), 2.93 (1H, ddd), 2.66-2.53 (2H, m).
$^{13}$C NMR (100.586 MHz, cd3od) δ 169.41, 135.14, 132.84, 129.55, 128.33, 59.09, 53.35, 52.81, 32.34.

Example 1

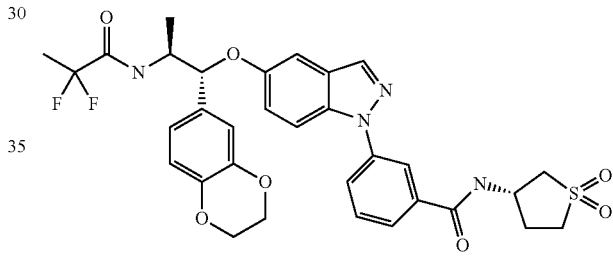

3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3S)-1,1-dioxidotetrahydrothiophen-3-yl]benzamide (E1)

3-(5-((1R,2S)-2-(2,2-difluoropropanamido)-1-(2,3-dihydrobenzo[b][1,4]dioxin-6-yl)propoxy)-1H-indazol-1-yl) benzoic acid (I4) (106 mg, 0.20 mmol), (S)-(-)-tetrahydrothiophene-3-amine-1,1-dioxide hydrochloride (I6) (40 mg, 0.23 mmol) and HBTU (95 mg, 0.25 mmol) in DMF (2 mL) was treated with DIEA (0.138 mL, 0.79 mmol). The reaction mixture was stirred at ambient temperature for 45 minutes. Water (10 mL) was added, the formed suspension was stirred for 1 hour. The solid was collected by filtration, washed with water and further purified by HPLC using an Kromasil 100-10-C18, 50×250 mm column, an 30 min gradient from 50% to 90% MeCN in water with flow=40 mL/min and UV=254 nm to collect fractions. Fractions containing the product was freeze dried, the resulting solid was dissolved in MeOH and iso-Hexane was added. The biphasic mixture was evaporated to give an solid that was suspended in iso-Hexane containing a small volume of EtOAc, the suspension was stirred at ambient temperature for 18 hours. The crystalline solid was collected by filtration, washed with iso-Hexane and dried. Yield 77 mg (59%).

APCI-MS: m/z 655 [MH$^+$]

¹H NMR (400 MHz, DMSO-d₆) δ 8.90 (1H, d), 8.65 (1H, d), 8.25 (1H, d), 8.19 (1H, s), 7.92 (1H, d), 7.86 (1H, d), 7.77 (1H, d), 7.68 (1H, t), 7.21 (1H, dd), 7.14 (1H, d), 6.89-6.78 (3H, m), 5.17 (1H, d), 4.73 (1H, m), 4.24-4.11 (5H, m), 3.52 (1H, dd), 3.37 (1H, m), 3.20 (1H, m), 3.10 dd), 2.45 (1H, m), 2.23 (1H, m), 1.55 (3H, t), 1.29 (3H, d).
LC (method A) rt=9.94 min
LC (method B) rt=9.15 min
Chiral SFC (method A) rt=4.93 min
M.p.=180° C.

The compounds of Examples 2 to 24 were prepared by processes analogous to those described in Example 1 or by processes known in the art.

Example 2

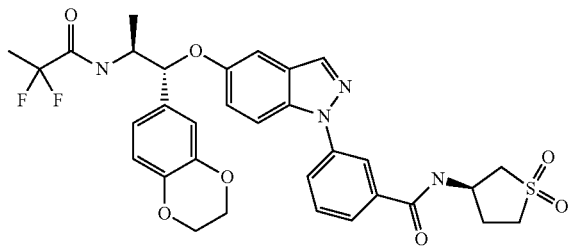 [SMILES: C[C@H](NC(=O)C(C)(F)F)[C@H](Oc1ccc2c(cnn2-c2cccc(C(=O)N[C@@H]3CCS(=O)(=O)C3)c2)c1)c1ccc2c(c1)OCCO2]

3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3R)-1,1-dioxidotetrahydrothiophen-3-yl]benzamide APCI-MS: m/z 655 [MH⁺]
¹H NMR (400 MHz, DMSO-d₆) δ 8.90 (1H, d), 8.65 (1H, d), 8.25 (1H, s), 8.19 (1H, s), 7.92 (1H, d), 7.85 (1H, d), 7.77 (1H, d), 7.68 (1H, t), 7.21 (1H, dd), 7.14 (1H, d), 6.89-6.78 (3H, m), 5.17 (1H, d), 4.72 (1H, m), 4.24-4.11 (5H, m), 3.52 (1H, dd), 3.38 (1H, m), 3.20 (1H, m), 3.10 (1H, dd), 2.44 (1H, m), 2.23 (1H, ddd), 1.55 (3H, t), 1.29 (3H, d).
LC (Method A) rt=9.94 min
LC (Method B) rt=9.15 min
Chiral SFC (method A) rt=5.87 min
M.p.=218° C.

Example 3

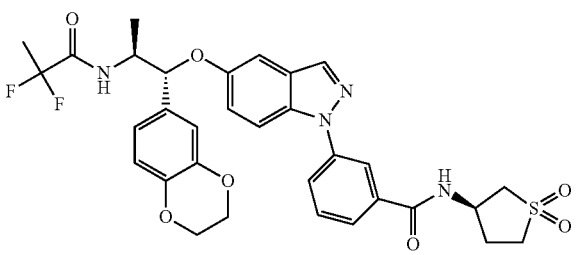 [SMILES: C[C@H](NC(=O)C(C)(F)F)[C@H](Oc1ccc2c(cnn2-c2cccc(C(=O)N[C@@H]3CCS(=O)(=O)C3)c2)c1)c1ccc2c(c1)OCCO2]

3-[5-({(1R,2S)-1-(4H-1,3-Benzodioxin-7-yl)-2-[(2,2-difluoropropanoyl)amino]propyl}oxy)-1H-indazol-1-yl]-N-[(3R)-1,1-dioxidotetrahydrothiophen-3-yl]benzamide APCI-MS: ink 655 [MH⁺]
¹H NMR (400 MHz, DMSO-d₆) δ 8.90 (1H, d), 8.71 (1H, d), 8.25 (1H, s), 8.18 (1H, s), 7.91 (1H, d), 7.86 (1H, d), 7.78 (1H, d), 7.68 (1H, t), 7.23 (1H, dd), 7.14 (1H, d), 7.00 (2H, q), 6.86 (1H, s), 5.26-5.17 (3H, m), 4.82 (2H, s), 4.78-4.67 (1H, m), 4.24-4.13 (1H, m), 3.52 (1H, dd), 3.42-3.32 (1H, m), 3.25-3.16 (1H, m), 3.10 (1H, dd), 2.49-2.41 (1H, m), 2.29-2.17 (1H, m), 1.56 (3H, t), 1.30 (3H, d).
LC (Method A, flow 1.0 mL/min) rt=10.15 min
LC (Method B, flow 1.0 mL/min) rt=9.76 min
M.p.=239° C.

Example 4

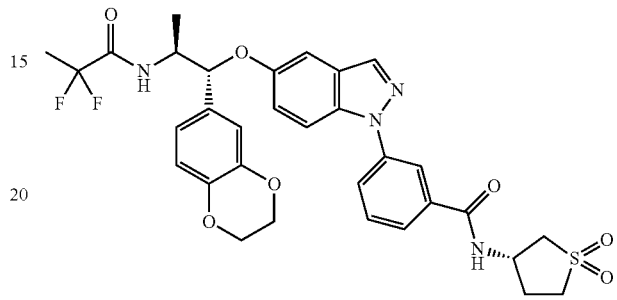

3-[5-({(1R,2S)-1-(4H-1,3-benzodioxin-7-yl)-2-[(2,2-difluoropropanoyl)amino]propyl}oxy)-1H-indazol-1-yl]-N-[(3S)-1,1-dioxidotetrahydrothiophen-3-yl]benzamide APCI-MS: m/z 655 [MH⁺]
¹H NMR (400 MHz, DMSO-d₆) δ 8.90 (1H, d), 8.71 (1H, d), 8.25 (1H, s), 8.18 (1H, s), 7.91 (1H, d), 7.85 (1H, d), 7.78 (1H, d), 7.68 (1H, t), 7.23 (1H, dd), 7.14 (1H, d), 7.00 (2H, q), 6.86 (1H, s), 5.26-5.17 (3H, m), 4.82 (2H, s), 4.78-4.67 (1H, m), 4.24-4.13 (1H, m), 3.52 (1H, dd), 3.42-3.32 (1H, m), 3.25-3.16 (1H, m), 3.10 (1H, dd), 2.49-2.41 (1H, m), 2.29-2.17 (1H, m), 1.56 (3H, t), 1.30 (3H, d).
LC (Method A, flow 1.0 mL/min) rt=9.80 min
LC (Method B, flow 1.0 mL/min) rt=8.76 min
M.p.=224° C.

Example 5

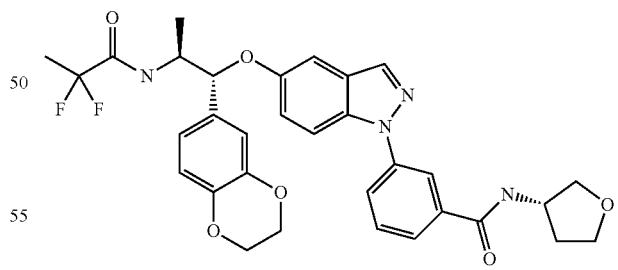

3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3S)-tetrahydrofuran-3-yl]benzamide APCI-MS: m/z 607 [MH⁺]
¹H NMR (400 MHz, DMSO-d₆) δ 8.71 (1H, d), 8.65 (1H, d), 8.24 (1H, s), 8.18 (1H, s), 7.90-7.84 (2H, m), 7.77 (1H, d), 7.65 (1H, t), 7.21 (1H, dd), 7.13 (1H, d), 6.89-6.78 (3H, m), 5.17 (1H, d), 4.48 (1H, m), 4.24-4.11 (5H, m), 3.90-3.81 (2H, m), 3.72 (1H, td), 3.61 (1H, dd), 2.16 (1H, m), 1.94 (1H, m), 1.55 (3H, t), 1.29 (3H, d).

LC (Method A) rt=12.02 min
LC (Method B) rt=11.12 min
Chiral SFC (method B) rt=5.10 min
M.p.=175° C.

Example 6

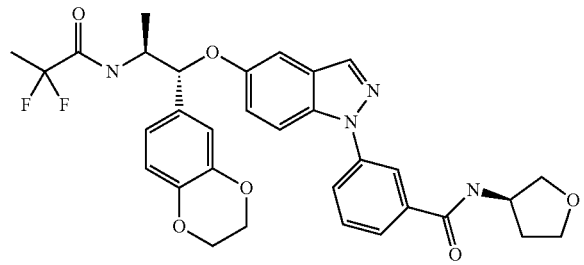 [SMILES: C[C@H](NC(=O)C(C)(F)F)[C@H](Oc1ccc2c(cnn2-c2cccc(C(=O)N[C@@H]3CCOC3)c2)c1)c1ccc2c(c1)OCCO2]

3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3R)-tetrahydrofuran-3-yl]benzamide APCI-MS: m/z 607 [MH$^+$]
$^1$H NMR (400 MHz, DMSO-d$_6$) δ 8.71 (1H, d), 8.65 (1H, d), 8.24 (1H, s), 8.18 (1H, s), 7.90-7.84 (2H, m), 7.77 (1H, d), 7.65 (1H, t), 7.21 (1H, dd), 7.13 (1H, d), 6.89-6.78 (3H, m), 5.17 (1H, d), 4.48 (1H, m), 4.23-4.10 (5H, m), 3.89-3.82 (2H, m), 3.72 (1H, td), 3.61 (1H, dd), 2.16 (1H, m), 1.94 (1H, m), 1.55 (3H, t), 1.29 (3H, d).

LC (method A) rt=12.03 min
LC (method B) rt=11.13 min
Chiral SFC (method B) rt=4.71 min
M.p.=177° C.

Example 7

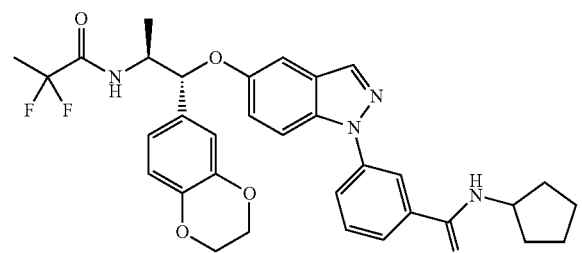

N-cyclopentyl-3-(5-{[(1R,2S)-2-[(2,2-difluoropropanoyl)amino]-1-(2,3-dihydro-1,4-benzodioxin-6-yl)propyl]oxy}-1H-indazol-1-yl)benzamide APCI-MS: m/z 605 [MH$^+$]
$^1$H-NMR (DMSO-d$_6$, 400 MHz) δ 8.65 (1H, d); 8.45 (1H, d); 8.24 (1H, d); 8.15 (1H, t); 7.86-7.83 (2H, m); 7.75 (1H, d); 7.63 (1H, t); 7.20 (1H, dd); 7.13 (1H, d); 6.88-6.85 (2H, m); 6.81-6.79 (1H, m); 5.17 (1H, d); 4.27-4.12 (6H, m); 1.93-1.85 (2H, m); 1.69 (2H, brs); 1.59-1.49 (7H, m); 1.29 (3H, d).

LC (method A) rt=14.40 min
LC (method B) rt=13.24 min
M.p.=170° C.

Example 8

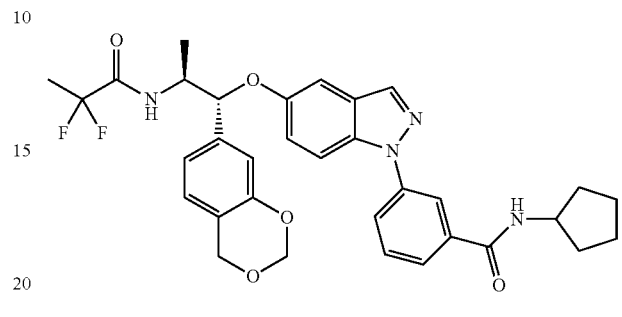

3-[5-({(1R,2S)-1-(4H-1,3-benzodioxin-7-yl)-2-[(2,2-difluoropropanoyl)amino]propyl}oxy)-1H-indazol-1-yl]-N-cyclopentylbenzamide APCI-MS: m/z 605 [MH$^+$]
$^1$H-NMR (DMSO-d$_6$, 400 MHz) δ 8.71 (1H, d); 8.45 (1H, d); 8.23 (1H, s); 8.14 (1H, t); 7.86-7.83 (2H, m); 7.75 (1H, d); 7.63 (1H, t); 7.22 (1H, dd); 7.13 (1H, d); 7.03-6.97 (2H, m); 6.86 (1H, s); 5.23-5.18 (3H, m); 4.82 (2H, s); 4.28-4.15 (2H, m); 1.95-1.86 (2H, m); 1.73-1.65 (2H, m); 1.60-1.50 (7H, m); 1.30 (3H, d).

LC (method A) rt=11.32 min
LC (method B) rt=10.47 min
M.p.=182° C.

Example 9

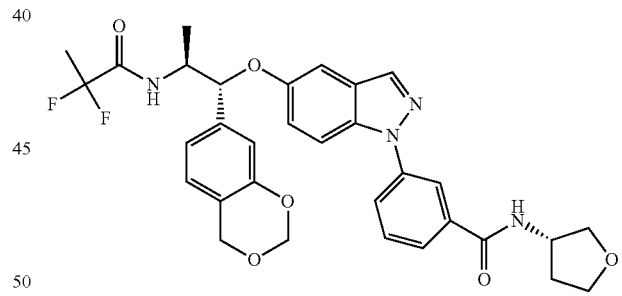

3-[5-({(1R,2S)-1-(4H-1,3-Benzodioxin-7-yl)-2-[(2,2-difluoropropanoyl)amino]propyl}oxy)-1H-indazol-1-yl]-N-[(3S)-tetrahydrofuran-3-yl]benzamide APCI-MS: m/z 607 [MH$^+$]
$^1$H NMR (400 MHz, DMSO-d$_6$) δ 8.74-8.67 (2H, m), 8.24 (1H, s), 8.18 (1H, s), 7.87 (2H, t), 7.77 (1H, d), 7.65 (1H, t), 7.22 (1H, dd), 7.13 (1H, d), 7.04-6.96 (2H, m), 6.86 (1H, s), 5.25-5.17 (3H, m), 4.82 (2H, s), 4.53-4.44 (1H, m), 4.24-4.13 (1H, m), 3.90-3.81 (2H, m), 3.75-3.68 (1H, m), 3.61 (1H, dd), 2.21-2.11 (1H, m), 1.99-1.89 (1H, m), 1.56 (3H, t), 1.30 (3H, d).

LC (method A) rt=11.88 min
LC (method B) rt=10.99 min
M.p.=192° C.

Example 10

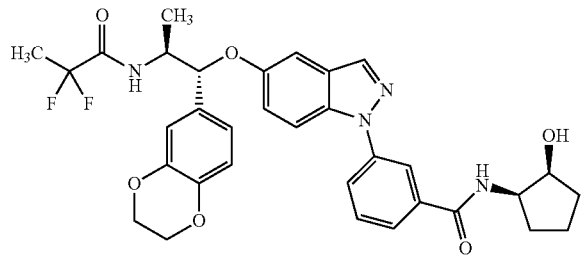 [SMILES: C[C@H](NC(=O)C(C)(F)F)[C@H](Oc1ccc2c(cnn2-c2cccc(C(=O)N[C@@H]3CCC[C@@H]3O)c2)c1)c1ccc2c(c1)OCCO2]

3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(1R,2S)-2-hydroxycyclopentyl]benzamide APCI-MS: m/z 621 [MH+]

1H NMR (300 MHz, DMSO-d$_6$, 1 proton signal covered by solvent) δ 8.65 (1H, d), 8.22 (2H, d), 8.10 (1H, d), 7.87 (2H, m), 7.78 (1H, d), 7.64 (1H, t), 7.20 (1H, dd), 7.13 (1H, d), 6.89-6.78 (3H, m), 5.17 (1H, d), 4.72 (1H, d), 4.21-4.03 (6H, m), 1.77 (4H, m), 1.55 (5H, t), 1.29 (3H, d).

LC (method A): rt=11.82 min
LC (method B): rt=9.86 min
M.p.=165° C.

Example 11

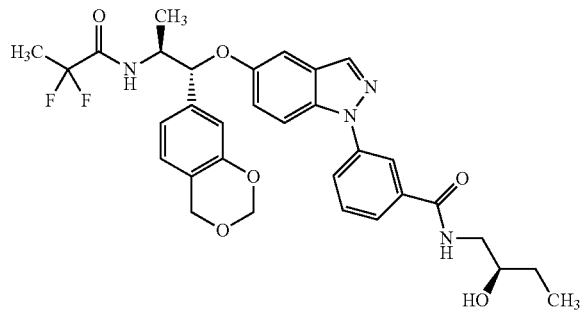 [SMILES: CC[C@@H](O)CNC(=O)c1cccc(-n2ncc3cc(O[C@H](c4ccc5c(c4)OCOC5)[C@H](C)NC(=O)C(C)(F)F)ccc32)c1]

3-[5-({(1R,2S)-1-(4H-1,3-benzodioxin-7-yl)-2-[(2,2-difluoropropanoyl)amino]propyl}oxy)-1H-indazol-1-yl]-N-[(2R)-2-hydroxybutyl]benzamide APCI-MS: m/z 609 [MH+]

1H NMR (400 MHz, DMSO-d$_6$) δ 8.71 (1H, d), 8.57 (1H, t), 8.24 (1H, s), 8.17 (1H, m), 7.86 (2H, m), 7.79 (1H, d), 7.64 (1H, t), 7.22 (1H, dd), 7.13 (1H, d), 7.04-6.96 (2H, m), 6.86 (1H, s), 5.26-5.18 (3H, m), 4.82 (2H, s), 4.72 (1H, d), 4.19 (1H, sext), 3.56 (1H, m), 3.37-3.27 (1H, partially obscured by solvent moisture signal), 3.23-3.14 (1H, m), 1.56 (3H, t), 1.47 (1H, m), 1.37-1.22 (1H, partially obscured by methyl doublet), 1.30 (3H, d), 0.90 (3H, t).

HPLC method (A): rt=11.83 min
HPLC method (B): rt=10.26 min
M.p.=182° C.

Example 12

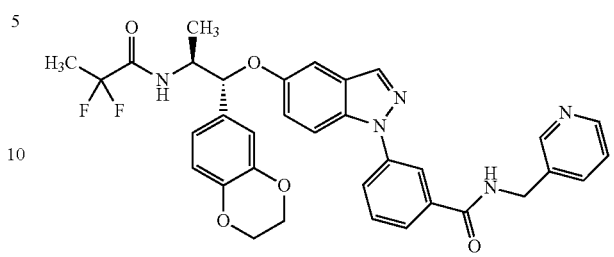

3-(5-{[(1R,2S)-2-[(2,2-difluoropropanoyl)amino]-1-(2,3-dihydro-1,4-benzodioxin-6-yl)-propyl]oxy}-1H-indazol-1-yl)-N-(pyridin-3-ylmethyl)benzamide APCI-MS: m/z 628 [MH+]

1H NMR (400 MHz, DMSO-d$_6$) δ 9.24 (1H, t), 8.66 (1H, d), 8.57 (1H, d), 8.46 (1H, dd), 8.24 (1H, s), 8.21 (1H, s), 7.89 (2H, m), 7.79 (1H, d), 7.74 (1H, m), 7.67 (1H, t), 7.36 (1H, dd), 7.21 (1H, dd), 7.14 (1H, d), 6.88-6.78 (3H, m), 5.17 (1H, d), 4.53 (2H, d), 4.25-4.09 (5H, m), 1.54 (3H, t), 1.29 (3H, d).

LC (method A) rt=9.61 min
LC (method B) rt=9.58 min
M.p.=135° C.

Example 13

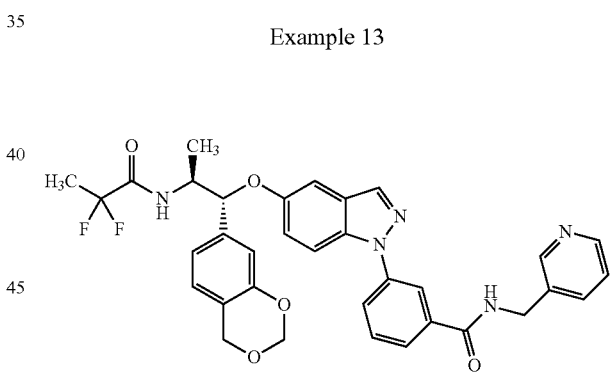

3-[5-({(1R,2S)-1-(4H-1,3-benzodioxin-7-yl)-2-[(2,2-difluoropropanoyl)amino]propyl}oxy)-1H-indazol-1-yl]-N-(pyridin-3-ylmethyl)benzamide APCI-MS: m/z 628 [MH+]

1H NMR (400 MHz, DMSO-d$_6$) δ 9.26 (1H, t), 8.71 (1H, d), 8.57 (1H, d), 8.46 (1H, dd), 8.24 (1H, s), 8.22-8.19 (1H, m), 7.89 (2H, t), 7.80 (1H, d), 7.76-7.72 (1H, m), 7.67 (1H, s), 7.36 (1H, dd), 7.22 (1H, dd), 7.13 (1H, d), 7.04-6.96 (2H, m), 6.86 (1H, s), 5.25-5.17 (3H, m), 4.82 (2H, s), 4.52 (2H, d), 4.24-4.13 (1H, m), 1.56 (3H, t), 1.30 (3H, d).

LC (method A) rt=9.86 min
LC (method B) rt=11.18 min
M.p.=159° C.

Example 14

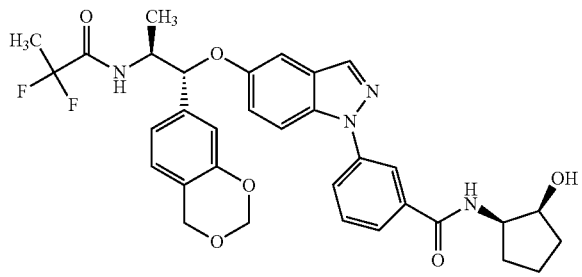 [SMILES: C[C@H](NC(=O)C(C)(F)F)[C@H](Oc1ccc2c(cnn2-c2cccc(C(=O)N[C@@H]3CCC[C@@H]3O)c2)c1)c1ccc2c(c1)OCOC2]

3-[5-({(1R,2S)-1-(4H-1,3-benzodioxin-7-yl)-2-[(2,2-difluoropropanoyl)amino]propyl}oxy)-1H-indazol-1-yl]-N-[(1R,2S)-2-hydroxycyclopentyl]benzamide APCI-MS: m/z 621 [MH+]

1H NMR (400 MHz, DMSO-d$_6$) δ 8.71 (1H, d), 8.23 (1H, s), 8.22 (1H, s), 8.10 (1H, d), 7.89-7.83 (2H, m), 7.78 (1H, d), 7.64 (1H, t), 7.22 (1H, dd), 7.13 (1H, d), 7.04-6.97 (2H, m), 6.86 (1H, s), 5.25-5.18 (3H, m), 4.82 (2H, s), 4.72 (1H, s), 4.24-4.14 (1H, m), 4.12-4.03 (2H, m), 1.89-1.69 (4H, m), 1.64-1.44 (5H, m), 1.30 (3H, d).

LC (method A) rt=12.19 min
LC (method B) rt=11.30 min
M.p.=165° C.

Example 15

Isomer 1

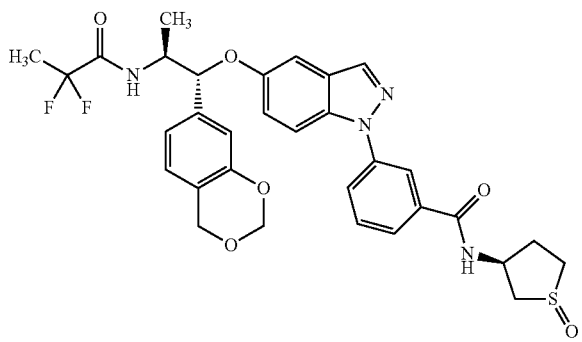

3-[5-({(1R,2S)-1-(4H-1,3-benzodioxin-7-yl)-2-[(2,2-difluoropropanoyl)amino]propyl}oxy)-1H-indazol-1-yl]-N-[(3S)-1-oxidotetrahydrothiophen-3-yl]benzamide (Isomer 1)

APCI-MS: m/z 639 [MH+]

1H NMR (400 MHz, DMSO-d$_6$) δ 8.88 (1H, d), 8.71 (1H, d), 8.24 (1H, s), 8.19 (1H, m), 7.89 (1H, d, further coupled), 7.85 (1H, d, further coupled), 7.78 (1H, d), 7.72 (1H, dd), 7.13 (1H, d), 7.02 (1H, d), 6.98 (1H, dd), 6.86 (1H, s), 5.26-5.17 (3H), 4.82 (2H, s), 4.66 (1H, sext.), 4.19 (1H, sext.), 3.54 (1H, dd), 3.01-2.86 (2H), 2.70 (1H, ddd), 2,59-~2-48 (1H, m, partially obscured by solvent signal), 2.43-2.34 (1H, m), 1.56 (3H, t), 1.30 (3H, d).

HPLC method (A): rt=10.65 min
HPLC method (B): rt=9.99 min
M.p.=196° C.

Example 16

Isomer 2

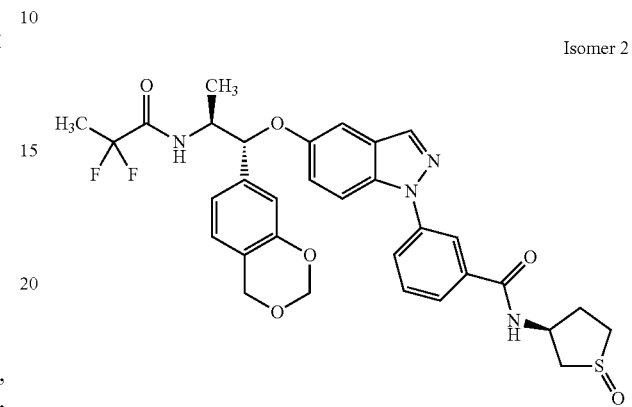

3-[5-({(1R,2S)-1-(4H-1,3-benzodioxin-7-yl)-2-[(2,2-difluoropropanoyl)amino]propyl}oxy)-1H-indazol-1-yl]-N-[(3S)-1-oxidotetrahydrothiophen-3-yl]benzamide (Isomer 2)

APCI-MS: m/z 639 [MH+]

1H NMR (400 MHz, DMSO-d$_6$) δ 8.74-8.67 (2H), 8.15 (1H, m), 7.89 (1H, d, further coupled), 7.84 (1H, d, further coupled), 7.77 (1H, d), 7.66 (1H, t), 7.22 (1H, dd), 7.13 (1H, d), 7.02 (1H, d) 6.98 (1H, dd), 6.86 (1H, s), 5.26-5.17 (3H), 5.01 (1H, sext.), 4.82 (2H, s), 4.19 (1H, sext, further coupled), 3.22 (1H, dt), 3.06 (2H, d), 2.82-2.74 (1H), 2.57 (1H, m), 2.14 (1H, m), 1.56 (3H, t), 1.30 (3H, d).

LC (method A): rt=10.40 min
LC (method B): rt=9.67 min
M.p.=202° C.

Example 17

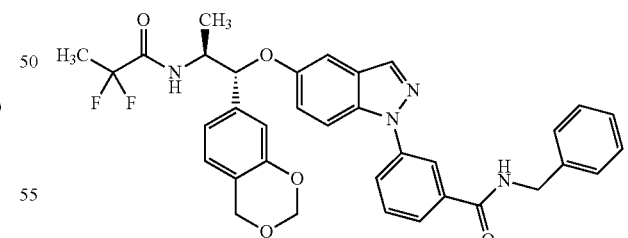

3-[5-({(1R,2S)-1-(4H-1,3-benzodioxin-7-yl)-2-[(2,2-difluoropropanoyl)amino]propyl}oxy)-1H-indazol-1-yl]-N-benzylbenzamide APCI-MS: m/z 627 [MH+]

1H-NMR (DMSO-d$_6$, 400 MHz); δ 9.22 (1H, t); 8.71 (1H, d); 8.24 (1H, s); 8.21 (1H, t); 7.89 (2H, dd); 7.79 (1H, d); 7.66 (1H, t); 7.32-7.31 (4H, m); 7.28-7.20 (2H, m); 7.13 (1H, d);

7.02-6.96 (2H, m); 6.86 (1H, s); 5.23-5.18 (3H, m); 4.82 (2H, s); 4.51 (2H, d); 4.22-4.15 (1H, m); 1.55 (3H, t); 1.30 (3H, d).
LC (method A) rt=14.42 min
LC (method B) rt=13.2 min
M.p.=174° C.

Example 18

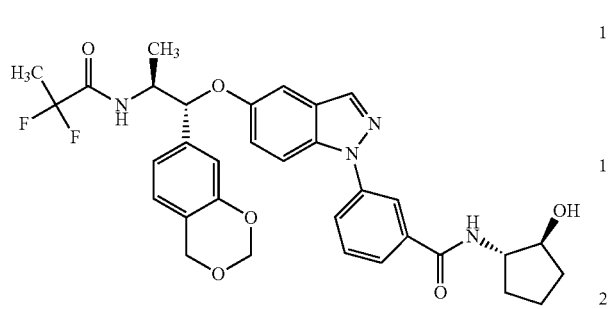

3-[5-({(1R,2S)-1-(4H-1,3-benzodioxin-7-yl)-2-[(2,2-difluoropropanoyl)amino]propyl}oxy)-1H-indazol-1-yl]-N-[(1S,2S)-2-hydroxycyclopentyl]benzamide APCI-MS: m/z 621 [MH+]
1H NMR (400 MHz, DMSO-d$_6$) δ 8.71 (1H, d), 8.39 (1H, d), 8.24 (1H, s), 8.17-8.14 (1H, m), 7.89-7.82 (2H, m), 7.76 (1H, d), 7.64 (1H, t), 7.22 (1H, dd), 7.13 (1H, d), 7.04-6.96 (2H, m), 6.86 (1H, s), 5.25-5.18 (3H, m), 4.82 (2H, s), 4.78 (1H, d), 4.24-4.13 (1H, m), 4.06-3.97 (2H, m), 2.06-1.96 (1H, m), 1.90-1.80 (1H, m), 1.71-1.42 (7H, m), 1.30 (3H, d).
LC (method A) rt=11.98 min
LC (method B) rt=11.21 min
M.p.=187° C.

Example 19

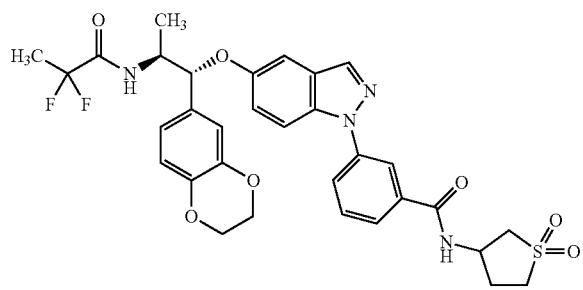 [SMILES: C[C@H](NC(=O)C(C)(F)F)[C@H](Oc1ccc2c(cnn2-c2cccc(C(=O)NC3CCS(=O)(=O)C3)c2)c1)c1ccc2c(c1)OCCO2]

3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3RS)-1,1-dioxidotetrahydrothiophen-3-yl]benzamide APCI-MS: m/z 655 [MH+]
1H NMR (400 MHz, DMSO-d$_6$) δ 1.29 (3H, d), 1.55 (3H, t), 2.18-2.29 (1H, m), 2.41-2.49 (1H, m), 3.10 (1H, dd), 3.15-3.26 (1H, m), 3.29-3.42 (1H, m), 3.52 (1H, dd), 4.11-4.23 (5H, m), 4.72 (1H, dd), 5.17 (1H, d), 6.78-6.82 (1H, m), 6.84-6.89 (2H, m), 7.14 (1H, d), 7.21 (1H, dd), 7.68 (1H, t), 7.77 (1H, d), 7.85 (1H, d), 7.89-7.93 (1H, m), 8.18 (1H, t), 8.25 (1H, d), 8.65 (1H, d), 8.90 (1H, d).

LC (method A) rt=10.31 min
LC (method B) rt=9.90 min
M.p.>150° C.

Example 20

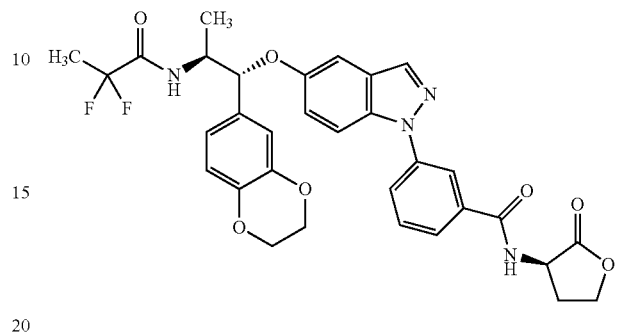

3-(5-{[(1R,2S)-2-[(2,2-difluoropropanoyl)amino]-1-(2,3-dihydro-1,4-benzodioxin-6-yl)propyl]oxy}-1H-indazol-1-yl)-N-[(3R)-2-oxotetrahydrofuran-3-yl]benzamide APCI-MS: m/z 621 [MH+]
1H NMR (400 MHz, DMSO-d$_6$) δ 1.30 (3H, d), 155 (3H, t), 2.30-2.42 (1H, m), 2.45-2.54 (1H, m), 4.11-4.24 (5H, m), 4.25-4.33 (1H, m), 4.43 (1H, td), 4.77-4.85 (1H, m), 5.17 (1H, d), 6.79-6.82 (1H, m), 6.84-6.89 (2H, m), 7.14 (1H, d), 7.22 (1H, dd), 7.69 (1H, t), 7.79 (1H, d), 7.86 (1H, d), 7.94 (1H, dd), 8.19 (1H, t), 8.26 (1H, d), 8.65 (1H, d), 9.17 (1H, d).
LC (method A) rt=10.4 min
LC (method B) rt=9.92 min
M.p.=183° C.

BIOLOGICAL EXPERIMENTAL

Human Glucocorticoid Receptor (GR) Assay

The radioligand GR binding assay is based on a competition assay using $^{3H}$-labeled Dexamethasone, Dexamethasone is known to bind in the ligand binding domain of GR and compete for binding with endogenous ligands like e.g. cortisol (Necela, 2003).

In the GR radioligand binding assay, test compounds were serially diluted in semi-log steps (10 concentrations) with a final concentration of 10 μM. Test compounds (1 μL) and controls (1 μL) in 100% DMSO were added to 96 Greiner V-bottom polypropylene plates. 0% control was 6.7% DMSO (final concentration in assay) and 100% control was 6.7 μM Dexamethasone.

The full length GR was diluted to a final concentration of 3.3% (0.495 mg/ml) in assay buffer (20 mM Tris-HCl, 1 mM EDTA, 10% (w/v) Glycerol, 20 mM Sodium molbydate, pH 7.4). 45 μL of GR was added to each well and the plates were incubated for 15 min at room temperature.

$^{3H}$-dexamethasone solution was diluted to a concentration of 70 nM in assay buffer (7 nM final assay concentration) and 5 μL was added to each well. The samples were mixed for 5 min using a plate shaker at 700 rpm, before incubation for 2 h at room temperature.

50 μL ice-cold charcoal solution (pH 7.4: 2% Charcoal, 0.2% Dextran T70 in 20 mM Tris-HCl, 1 mM EDTA and 20 mM Sodium molbydate) was'added to each well and the samples were mixed on plate shaker for 5 minutes.

The plate was then centrifuged for 1.5 min at 1500 rpm, the samples (80 μL) were transferred from each well to a filter plate (Millipore, 0.45 μm, MHVBN45) on a vacuum manifold and then collected into new plates (Greiner, 96 well white/transparent, 655095). The filter plate was washed once with 20 μl of water and then 100 μL of scintillation liquid was added to each well and mixed by incubation on plate shaker for 5 min. Radioactivity was measured in a 1450 Microbeta Trilux Reader (Wallac) counting cpm for 2 minutes per well. The data obtained from each replicate experiment were analysed using the software ActivityBase, version 5.4.3 (ID Business Solutions Ltd) and $IC_{50}$ values were calculated. Ref: Necela, B M, Cidlowski, J A, Trends Pharmacol Sci, 24: 58, 2003

Transrepression Reporter Gene Assay

The human bronchogenic carcinoma cell-line, ChaGo-K-1 (ATCC: HTB 168), were transfected with 5×TRE-LacZ (clone 16:15:5 s5), i.e. TRE transfected cells, to measure transrepression activity of the selected compounds. Before use, the cells were grown for one to two weeks in selection medium containing 0.7 mg geneticin (G418)/ml medium. The cells were cultured at 37° C., 5% $CO_2$ and 100% humidity in 96 well microtiter plates in RPMI-medium complemented with 10% fetal calf serum, 1% non-essential amino acids and 1% sodium pyruvate. The cells were passaged once weekly.

The TRE transfected cells were seeded in 96 well plates with 25-30 000 cells/well and grown for 72-96 h, to reach about 80% confluence. To stimulate the upregulation of the AP-1/TRE-activity, the cells were stimulated with 10 ng/ml Phorbol Myristate acetate (PMA) 3-5 h prior to addition of compounds. The PMA was present during the whole experiment. The TRE mediated effects (transrepression) in the transfected ChagGo-K-1 cells was measured as downregulation of β-galactosidase activity. The β-galactosidase activity for the transrepression experiments was measured by a fluorometric assay performed in microtiter plates. Cells were washed once in PBS. 180 μl of a reaction mixture containing 5 parts of Z-buffer and one part 4-methylumbelliferyl-β-D-galactosidase (MUG)-solution was then added (150 μl Z-buffer [18 μl 0.6 M $Na_2HPO_4$, 12 μl 0.6 M $NaH_2PO_4$, 7.2 μl 0.25 M KCl, 18 μl 0.01 M $MgSO_4$, 1.8 μl 10% Triton X-100, 93 μl $H_2O$]+30 μl 3 mM 4-methylumbelliferyl-γ-D-galactosidase). After 60 min incubation at 37° C., 70 μl stop buffer was added to each well and the fluorescence was read in a fluorometer (Spectramax Gemini) with emission filter at 460 nm and excitation filter at 360 nm. The TRE activity was calculated as the relative activity compared to cells not treated with compounds. Inhibition of β-galactosidase by the compounds is expressed as percent inhibition compared to Dexamethasone $10^{-6}$ M set as a 100 percent control within each experiment and DMSO 0.1% set as background control. The effect of Dexamethasone is well documented in this system and was therefore chosen as a positive control for comparison of the potency and efficacy of the compounds.

TABLE 1

Binding data, melting point and crystallinity for the examplified compounds.

| Example Nr | GR Hu Bind Filter Mean Control IC50 [nM] | Max Melting Onset Temperature (° C.) | Crystallinity | Agonism TRE IC50 [nM] |
|---|---|---|---|---|
| 1 | 1.32 | 180 | Crystalline | 0.212 |
| 2 | 1.36 | 218 | Crystalline | 0.163 |
| 3 | 1.60 | 239 | Crystalline | 0.344 |
| 4 | 1.40 | 224 | Crystalline | 0.733 |
| 5 | 1.08 | 175 | Crystalline | 0.0514 |
| 6 | 0.913 | 177 | Crystalline | 0.0518 |
| 7 | 1.30 | 170 | Crystalline | 0.163 |
| 8 | 0.796 | 182 | Crystalline | 0.388 |
| 9 | 1.09 | 192 | Crystalline | 0.191 |
| 10 | 0.647 | 165 | Crystalline | 0.112 |
| 11 | 2.15 | 182 | Crystalline | 0.517 |
| 12 | 0.767 | 135 | Crystalline | 0.0367 |
| 13 | 0.817 | 159 | Crystalline | 0.0238 |
| 14 | 1.75 | 165 | Crystalline | 0.145 |
| 15 | 3.64 | 196 | Crystalline | 0.499 |
| 16 | 4.27 | 202 | Crystalline | 0.6 |
| 17 | 0.996 | 174 | Crystalline | 0.754 |
| 18 | 3.44 | 187 | Crystalline | 0.552 |
| 19 | 0.663 | >150 | Crystalline | 0.159 |
| 20 | 1.96 | 183 | Crystalline | 0.92 |

The invention claimed is:

1. A compound which is of the formula:

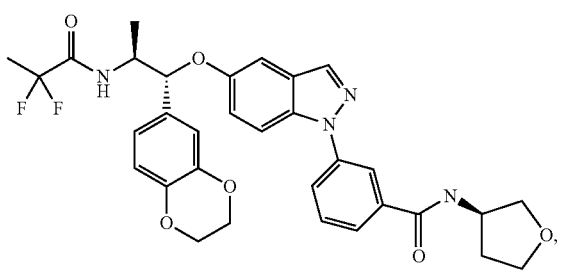 [SMILES: C[C@H](NC(=O)C(C)(F)F)[C@H](Oc1ccc2c(cnn2-c2cccc(C(=O)N[C@@H]3CCOC3)c2)c1)c1ccc2c(c1)OCCO2]

or a pharmaceutically acceptable salt thereof.

2. A compound which is of the formula:

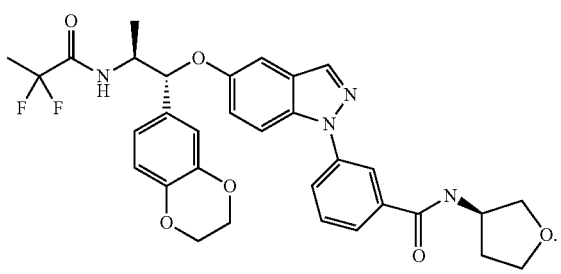 [SMILES: C[C@H](NC(=O)C(C)(F)F)[C@H](Oc1ccc2c(cnn2-c2cccc(C(=O)N[C@@H]3CCOC3)c2)c1)c1ccc2c(c1)OCCO2]

3. A pharmaceutical composition, wherein the composition comprises:

the compound according to claim 1 or a pharmaceutically acceptable salt thereof; and a pharmaceutically acceptable adjuvant, diluent or carrier.

4. A pharmaceutical composition, wherein the composition comprises:

the compound according to claim 2; and a pharmaceutically acceptable adjuvant, diluent or carrier.

* * * * *